US007677411B2

(12) United States Patent
Crowder et al.

(10) Patent No.: US 7,677,411 B2
(45) **Date of Patent: *Mar. 16, 2010**

(54) APPARATUS, SYSTEMS AND RELATED METHODS FOR PROCESSING, DISPENSING AND/OR EVALUATINGL DRY POWDERS

(75) Inventors: Timothy M. Crowder, Durham, NC (US); Anthony J. Hickey, Chapel Hill, NC (US); Vanessa Boekestein, Lexington Park, MD (US)

(73) Assignee: Oriel Therapeutics, Inc., Durham, NC (US)

( * ) Notice: Subject to any disclaimer, the term of this patent is extended or adjusted under 35 U.S.C. 154(b) by 1796 days.

This patent is subject to a terminal disclaimer.

(21) Appl. No.: 10/606,676

(22) Filed: Jun. 26, 2003

(65) Prior Publication Data

US 2004/0055598 A1 Mar. 25, 2004

Related U.S. Application Data

(63) Continuation-in-part of application No. 10/434,009, filed on May 8, 2003, now Pat. No. 6,889,690.

(60) Provisional application No. 60/440,513, filed on Jan. 16, 2003, provisional application No. 60/392,671, filed on Jun. 27, 2002, provisional application No. 60/379,521, filed on May 10, 2002.

(51) Int. Cl.
*B67B 7/00* (2006.01)

(52) U.S. Cl. ............................ 222/1; 222/52; 222/161; 222/181.1; 222/185.1; 222/196; 198/533; 700/231

(58) Field of Classification Search ..................... 222/1, 222/63, 161, 164–166, 196, 196.1, 200–203, 222/185.1, 198, 181.1, 52; 128/203.15; 310/311, 310/313 R, 313 A, 318, 322, 330, 334, 317, 310/323.06, 316.01–316.03; 700/231, 244, 700/263, 240; 198/533
See application file for complete search history.

(56) References Cited

U.S. PATENT DOCUMENTS

| | | | | |
|---|---|---|---|---|
| 3,565,070 | A | 2/1971 | Hanson et al. | |
| 3,679,010 | A | 7/1972 | Bullivant | 177/16 |
| 3,724,720 | A | 4/1973 | Bullivant | 222/55 |
| 3,777,874 | A | 12/1973 | Birckhead | 406/32 |
| 3,812,854 | A | 5/1974 | Michaels et al. | |
| 3,948,264 | A | 4/1976 | Wilke et al. | |

(Continued)

FOREIGN PATENT DOCUMENTS

| | | |
|---|---|---|
| DE | 1907444 | 9/1970 |

(Continued)

OTHER PUBLICATIONS

Brown et al., "*Piezo-Electronic Inhaler*", Drug Delivery Technology, vol. 4, No. 8, pp. 90-93, Oct. 2004.

(Continued)

*Primary Examiner*—Frederick C. Nicolas
(74) *Attorney, Agent, or Firm*—Myers Bigel Sibley & Sajovec, P.A.

(57) ABSTRACT

Methods, systems, and computer program products flowably process dry powders using a non-linear vibratory signal individualized or customized to a target dry powder undergoing processing to facilitate fluidic flow through a flow channel.

9 Claims, 16 Drawing Sheets

U.S. PATENT DOCUMENTS

| | | | | |
|---|---|---|---|---|
| 3,962,917 | A | 6/1976 | Terada | |
| 3,971,377 | A | 7/1976 | Damani | |
| 3,989,042 | A | 11/1976 | Mitsui et al. | |
| 4,054,784 | A | 10/1977 | Ricciardi et al. | 700/240 |
| 4,113,809 | A | 9/1978 | Abair et al. | |
| 4,147,166 | A | 4/1979 | Hansen | |
| 4,319,155 | A | 3/1982 | Nakai et al. | 310/316 |
| 4,381,545 | A | 4/1983 | Biddle et al. | 700/240 |
| 4,393,884 | A | 7/1983 | Jacobs | |
| 4,446,862 | A | 5/1984 | Baum et al. | |
| 4,472,091 | A | 9/1984 | Callahan | 406/132 |
| 4,600,855 | A | 7/1986 | Strachan | |
| 4,607,254 | A | 8/1986 | Carlson | |
| 4,648,393 | A | 3/1987 | Landis et al. | |
| 4,778,054 | A | 10/1988 | Newell et al. | 206/531 |
| 4,819,629 | A | 4/1989 | Jonson | |
| 4,836,417 | A | 6/1989 | Uchiyama et al. | |
| 4,877,989 | A | 10/1989 | Drews et al. | |
| 5,063,922 | A | 11/1991 | Hakkinen | |
| 5,349,947 | A | 9/1994 | Newhouse et al. | 128/203.21 |
| 5,363,842 | A | 11/1994 | Mishelevich et al. | |
| 5,388,572 | A | 2/1995 | Mulhauser et al. | 128/203.15 |
| 5,437,271 | A | 8/1995 | Hodson et al. | 128/203.15 |
| 5,469,843 | A | 11/1995 | Hodson | 128/203.15 |
| 5,482,030 | A | 1/1996 | Klein | 128/200.23 |
| 5,482,032 | A | 1/1996 | Smith et al. | 128/203.15 |
| 5,497,764 | A | 3/1996 | Ritson et al. | 128/200.14 |
| 5,505,196 | A | 4/1996 | Herold et al. | 128/203.15 |
| 5,507,277 | A | 4/1996 | Rubsamen et al. | 128/200.14 |
| 5,509,404 | A | 4/1996 | Lloyd et al. | 128/200.14 |
| 5,520,166 | A | 5/1996 | Ritson et al. | 128/200.14 |
| 5,522,378 | A | 6/1996 | Ritson et al. | 128/200.14 |
| 5,522,385 | A | 6/1996 | Lloyd et al. | 128/203.26 |
| 5,542,410 | A | 8/1996 | Goodman et al. | 128/200.14 |
| 5,544,646 | A | 8/1996 | Lloyd et al. | 128/200.14 |
| 5,558,085 | A | 9/1996 | Rubsamen et al. | 128/200.14 |
| 5,577,497 | A | 11/1996 | Mecikalski et al. | 128/203.15 |
| 5,583,304 | A | 12/1996 | Kalidindi | |
| 5,608,647 | A | 3/1997 | Rubsamen et al. | 364/509 |
| 5,618,177 | A | 4/1997 | Abbott | 433/88 |
| 5,622,166 | A | 4/1997 | Eisele et al. | 128/203.12 |
| 5,642,727 | A | 7/1997 | Datta et al. | 128/203.15 |
| 5,655,523 | A | 8/1997 | Hodson et al. | 128/315 |
| 5,660,166 | A | 8/1997 | Lloyd et al. | 128/200.14 |
| 5,672,581 | A | 9/1997 | Rubsamen et al. | 514/3 |
| 5,694,919 | A | 12/1997 | Rubsamen et al. | 128/200.14 |
| 5,694,920 | A | 12/1997 | Abrams et al. | 128/200.16 |
| 5,699,789 | A | 12/1997 | Hendricks | 128/203.15 |
| 5,709,202 | A | 1/1998 | Lloyd et al. | 128/200.14 |
| 5,718,222 | A | 2/1998 | Lloyd et al. | 128/200.14 |
| 5,724,957 | A | 3/1998 | Rubsamen et al. | 128/200.14 |
| 5,724,959 | A | 3/1998 | McAughey et al. | 128/203.15 |
| 5,727,546 | A | 3/1998 | Clarke et al. | 128/203.15 |
| 5,735,263 | A | 4/1998 | Rubsamen et al. | 128/200.14 |
| 5,740,793 | A | 4/1998 | Hodson et al. | 128/203.15 |
| 5,743,250 | A | 4/1998 | Gonda et al. | 128/200.14 |
| 5,743,252 | A | 4/1998 | Rubsamen et al. | 128/200.14 |
| 5,755,218 | A | 5/1998 | Johansson et al. | 128/200.14 |
| 5,767,068 | A | 6/1998 | VanDevanter et al. | 514/9 |
| 5,770,152 | A | 6/1998 | Schuster et al. | 422/73 |
| 5,792,057 | A | 8/1998 | Rubsamen et al. | 600/431 |
| 5,813,397 | A | 9/1998 | Goodman et al. | 128/200.14 |
| 5,819,726 | A | 10/1998 | Rubsamen et al. | 128/200.14 |
| 5,823,178 | A | 10/1998 | Lloyd et al. | 128/200.14 |
| 5,823,434 | A | 10/1998 | Cooper | 239/102.2 |
| 5,826,570 | A | 10/1998 | Goodman et al. | 128/200.14 |
| 5,829,435 | A | 11/1998 | Rubsamen et al. | 128/203.21 |
| 5,829,436 | A | 11/1998 | Rubsamen et al. | 128/200.14 |
| 5,855,564 | A | 1/1999 | Ruskewicz et al. | 604/62 |
| 5,857,456 | A | 1/1999 | Sun et al. | 128/203.15 |
| 5,871,010 | A | 2/1999 | Datta et al. | 128/203.15 |
| 5,873,358 | A | 2/1999 | Gonda et al. | 128/200.14 |
| 5,875,776 | A | 3/1999 | Vaghefi | 128/203.15 |
| 5,884,620 | A | 3/1999 | Gonda et al. | 128/200.14 |
| 5,888,477 | A | 3/1999 | Gonda et al. | 424/45 |
| 5,894,841 | A | 4/1999 | Voges | 128/203.12 |
| 5,906,202 | A | 5/1999 | Schuster et al. | 128/203.23 |
| 5,906,294 | A | 5/1999 | Ikeya et al. | 222/55 |
| D410,541 | S | 6/1999 | Moulin | D24/110 |
| 5,910,301 | A | 6/1999 | Farr et al. | 424/45 |
| 5,915,378 | A | 6/1999 | Lloyd et al. | 128/200.22 |
| 5,921,237 | A | 7/1999 | Eisele et al. | 128/203.21 |
| 5,934,272 | A | 8/1999 | Lloyd et al. | 239/200.22 |
| 5,938,075 | A | 8/1999 | Murai et al. | 222/1 |
| 5,938,118 | A | 8/1999 | Cooper | 239/102.2 |
| 5,941,240 | A | 8/1999 | Gonda et al. | 128/200.14 |
| 5,955,705 | A | 9/1999 | Germanton | |
| 5,957,124 | A | 9/1999 | Lloyd et al. | 128/200.22 |
| 5,960,609 | A | 10/1999 | Abrams et al. | 53/428 |
| 5,960,792 | A | 10/1999 | Lloyd et al. | 128/203.22 |
| 5,970,973 | A | 10/1999 | Gonda et al. | 128/200.14 |
| 5,971,951 | A | 10/1999 | Ruskewicz et al. | 604/62 |
| 5,975,076 | A | 11/1999 | Yianneskis et al. | 128/203.15 |
| 5,993,783 | A | 11/1999 | Eljamal et al. | 424/46 |
| 6,012,450 | A | 1/2000 | Rubsamen | 128/200.14 |
| 6,012,454 | A | 1/2000 | Hodson et al. | 128/203.15 |
| 6,014,969 | A | 1/2000 | Lloyd et al. | 128/200.14 |
| 6,024,090 | A | 2/2000 | Gonda et al. | 128/204.23 |
| 6,026,809 | A | 2/2000 | Abrams et al. | 125/203.15 |
| 6,051,551 | A | 4/2000 | Hughes et al. | 514/3 |
| 6,056,027 | A | 5/2000 | Patterson | |
| 6,057,515 | A | 5/2000 | Murai et al. | 177/116 |
| 6,062,214 | A | 5/2000 | Howlett | 128/200.23 |
| 6,063,138 | A | 5/2000 | Hanna et al. | 23/295 R |
| 6,065,509 | A | 5/2000 | Bonney et al. | 141/71 |
| 6,070,575 | A | 6/2000 | Gonda et al. | 128/203.12 |
| 6,080,762 | A | 6/2000 | Allen et al. | 514/337 |
| 6,085,753 | A | 7/2000 | Gonda et al. | 128/898 |
| 6,089,227 | A | 7/2000 | Nilsson | 128/203.15 |
| 6,095,134 | A | 8/2000 | Sievers et al. | 128/200.14 |
| 6,095,141 | A | 8/2000 | Armer et al. | 128/204.26 |
| 6,095,142 | A | 8/2000 | Giorgini | 128/205.23 |
| 6,098,615 | A | 8/2000 | Lloyd et al. | 128/200.14 |
| 6,098,620 | A | 8/2000 | Lloyd et al. | 128/204.23 |
| 6,102,035 | A | 8/2000 | Asking et al. | 128/203.15 |
| 6,109,261 | A | 8/2000 | Clarke et al. | 128/203.15 |
| 6,116,238 | A | 9/2000 | Jackson et al. | 128/203.15 |
| 6,119,953 | A | 9/2000 | Gañán-Calvo et al. | 239/8 |
| 6,123,068 | A | 9/2000 | Lloyd et al. | 128/200.24 |
| 6,131,567 | A | 10/2000 | Gonda et al. | 128/200.14 |
| 6,131,570 | A | 10/2000 | Schuster et al. | 128/203.26 |
| 6,142,146 | A | 11/2000 | Abrams et al. | 128/203.15 |
| 6,143,277 | A | 11/2000 | Ashurst et al. | 424/45 |
| 6,152,130 | A | 11/2000 | Abrams et al. | 128/204.21 |
| 6,167,880 | B1 | 1/2001 | Gonda et al. | 128/200.14 |
| 6,182,655 | B1 | 2/2001 | Keller et al. | 128/203.15 |
| 6,192,876 | B1 | 2/2001 | Denyer et al. | 125/205.25 |
| 6,192,882 | B1 | 2/2001 | Gonda | 128/203.21 |
| 6,196,218 | B1 | 3/2001 | Voges | 128/200.14 |
| 6,208,065 | B1 | 3/2001 | Ueyama | 310/328 |
| 6,209,538 | B1 | 4/2001 | Casper et al. | 128/203.15 |
| 6,230,706 | B1 | 5/2001 | Gonda et al. | 128/203.12 |
| 6,237,590 | B1 | 5/2001 | Leedom et al. | 128/203.15 |
| 6,250,298 | B1 | 6/2001 | Gonda et al. | 128/200.14 |
| 6,263,872 | B1 | 7/2001 | Schuster et al. | 128/203.26 |
| 6,271,206 | B1 | 8/2001 | Pillai et al. | 514/44 |
| 6,288,360 | B1 | 9/2001 | Beste | 219/121.71 |
| 6,295,986 | B1 | 10/2001 | Patel et al. | 128/203.12 |
| 6,296,152 | B1 * | 10/2001 | Semenenko | 222/199 |
| 6,328,033 | B1 | 12/2001 | Avrahami | 128/203.15 |
| 6,335,316 | B1 | 1/2002 | Hughes et al. | 514/12 |
| 6,348,209 | B2 | 2/2002 | Placke et al. | 624/435 |
| 6,349,719 | B2 | 2/2002 | Gonda | 128/200.14 |
| 6,351,984 | B1 | 3/2002 | Srinivasan | 73/40.7 |

| | | | | |
|---|---|---|---|---|
| 6,351,987 | B1 | 3/2002 | Winston et al. | 73/53.01 |
| 6,354,516 | B1 | 3/2002 | Patel et al. | 239/331 |
| 6,369,354 | B1 | 4/2002 | Beste | 219/121.71 |
| 6,488,181 | B1 * | 12/2002 | Schuller et al. | 222/161 |
| 6,651,341 | B1 | 11/2003 | Myrman | 30/2 |
| 6,805,175 | B1 | 10/2004 | Pinkas et al. | 141/130 |
| 6,964,550 | B2 | 11/2005 | Hafner | |
| 6,985,798 | B2 | 1/2006 | Crowder et al. | |
| 7,118,010 | B2 * | 10/2006 | Crowder et al. | 222/1 |
| 7,428,446 | B2 * | 9/2008 | Crowder et al. | 700/240 |
| 2001/0007853 | A1 | 7/2001 | Dimarchi et al. | 514/3 |
| 2001/0053761 | A1 | 12/2001 | Dimarchi et al. | 514/3 |
| 2004/0153262 | A1 | 8/2004 | Crowder et al. | |
| 2005/0126569 | A1 | 6/2005 | Crowder et al. | |
| 2005/0267628 | A1 | 12/2005 | Crowder et al. | |

FOREIGN PATENT DOCUMENTS

| | | | |
|---|---|---|---|
| DE | 4328750 | | 12/1994 |
| EP | 0129985 | | 1/1985 |
| EP | 0282958 | | 9/1988 |
| EP | 1106196 | A | 6/2001 |
| EP | 1166812 | A | 1/2002 |
| EP | 1172122 | A1 | 1/2002 |
| EP | 1021335 | B1 | 6/2003 |
| GB | 1401446 | | 7/1975 |
| JP | 58-067330 | | 4/1983 |
| JP | 02132011 | | 5/1990 |
| JP | 11208891 | | 3/1999 |
| JP | 2000326901 | | 11/2000 |
| JP | 2001095896 | | 4/2001 |
| JP | 2001097532 | | 4/2001 |
| JP | 2001215146 | | 8/2001 |
| WO | WO 97/05018 | | 2/1997 |
| WO | WO99/19215 | | 4/1999 |
| WO | WO99/65551 | | 12/1999 |
| WO | WO 01/68169 | A | 9/2001 |
| WO | WO2004/002827 | A1 | 1/2004 |

OTHER PUBLICATIONS

PCT International Search Report, International Application No. PCT/US03/20842 filed Jun. 26, 2003; mailed Aug. 23, 2003.

PCT International Search Report, International Application No. PCT/US03/20843 filed Jun. 26, 2003; mailed Aug. 23, 2003.

PCT International Search Report, International Application No. PCT/US03/20976 filed Jun. 26, 2003; mailed Aug. 23, 2003.

Crowder, et al., 2001: *an Odyssey in Inhaler Formulation and Design*, Pharmaceutical Technology, pp. 99-113, Jul. 2001.

Peart et al., *New Developments in Dry Powder Inhaler Technology*, American Pharmaceutical Review, vol. 4, n.3, pp. 37-45 (2001).

Prime et al., *Review of Dry Powder Inhalers*, 26 Adv. Drug Delivery Rev., pp. 51-58 (1997).

Hickey et al., *A new millennium for inhaler technology*, 21 Pharm. Tech., n.6, pp. 116-125 (1997).

http://advair.ibreathe.com/consumer/2_2_2_taking_advair_animation.htm, Advair DISKUS 100/50, 3 sheets, 1997.

PCT International Search Report, International Application No. PCT/US03/14619 mailed Dec. 23, 2003.

Crowder, T.M., *Precision powder metering utilizing fundamental powder flow characteristics*, ScienceDirect Powder Technology 173 (2007), pp. 217-223.

Crowder et al., *Powder specific active dispersion for generation of pharmaceutical aerosols*, ScienceDirect International Journal of Pharmaceutics 327 (2006) pp. 65-72.

Japanese Office Action for Japanese Application No. 2004-549853, received Aug. 17, 2009.

Supplementary European Search Report for corresponding EP application No. 03762332, dated Oct. 1, 2009.

* cited by examiner

```
                    ┌─────────────────────────┐
                    │   GENERATING A POWDER-  │
                    │ SPECIFIC VIBRATORY ENERGY│
       ┌────────────│  SIGNAL TO A DRY POWDER │────────────┐
       │            │     BEING DISPENSED.    │            │
       │            │           100           │            │
       ▼            └─────────────────────────┘            ▼
```

┌─────────────────────────┐                    ┌─────────────────────────┐
│ THE POWDER-SPECIFIC SIGNAL│                  │      THE SYSTEM CAN BE    │
│    IS A NON-LINEAR MULTI- │                  │   CONFIGURED TO ADJUST ITS│
│      FREQUENCY SIGNAL.    │                  │  SIGNAL TO GENERATE MULTIPLE│
│            110            │                  │  DIFFERENT POWDER-SPECIFIC │
└─────────────────────────┘                    │   SIGNALS, CORRESPONDING TO│
                                               │  THE PARTICULAR POWDER BEING│
                                               │         DISPENSED.          │
                                               │            115              │
                                               └─────────────────────────┘

┌─────────────────────────┐
                    │   FLOWABLY DISPENSING   │
                    │   SUCCESSIVE METED      │
                    │  QUANTITIES OF DRY POWDER│
                    │  USING THE POWDER-SPECIFIC│
                    │          SIGNAL.         │
                    │            120           │
                    └─────────────────────────┘

┌─────────────────────────┐
│   THE DRY POWDER IS A LOW-│
│ DENSITY PHARMACOLOGICALLY │
│    ACTIVE DRY POWDER.     │
│            122            │
└─────────────────────────┘

┌─────────────────────────┐
                    │  CAPTURING THE SUCCESSIVE│
                    │  METED QUANTITIES OF DRY │
                    │   POWDER IN A DESIRED    │
                    │    RECEIVING MEMBER.     │
                    │            130           │
                    └─────────────────────────┘

┌─────────────────────────┐              ┌─────────────────────────┐
│   THE METED QUANTITY CAN BE│            │   THE AMOUNT OF DISPENSED│
│   A UNIT DOSE AMOUNT OF LESS│           │   DRY POWDER CAN BE TIME-│
│    THAN ABOUT 15mg AND THE │            │        CONTROLLED.       │
│   DISPENSING CAN BE CARRIED│            │            131           │
│     OUT WITH A DOSE-DOSE   │            └─────────────────────────┘
│  VARIABILITY OF LESS THAN ABOUT│
│             5-10%          │
│             124            │
└─────────────────────────┘

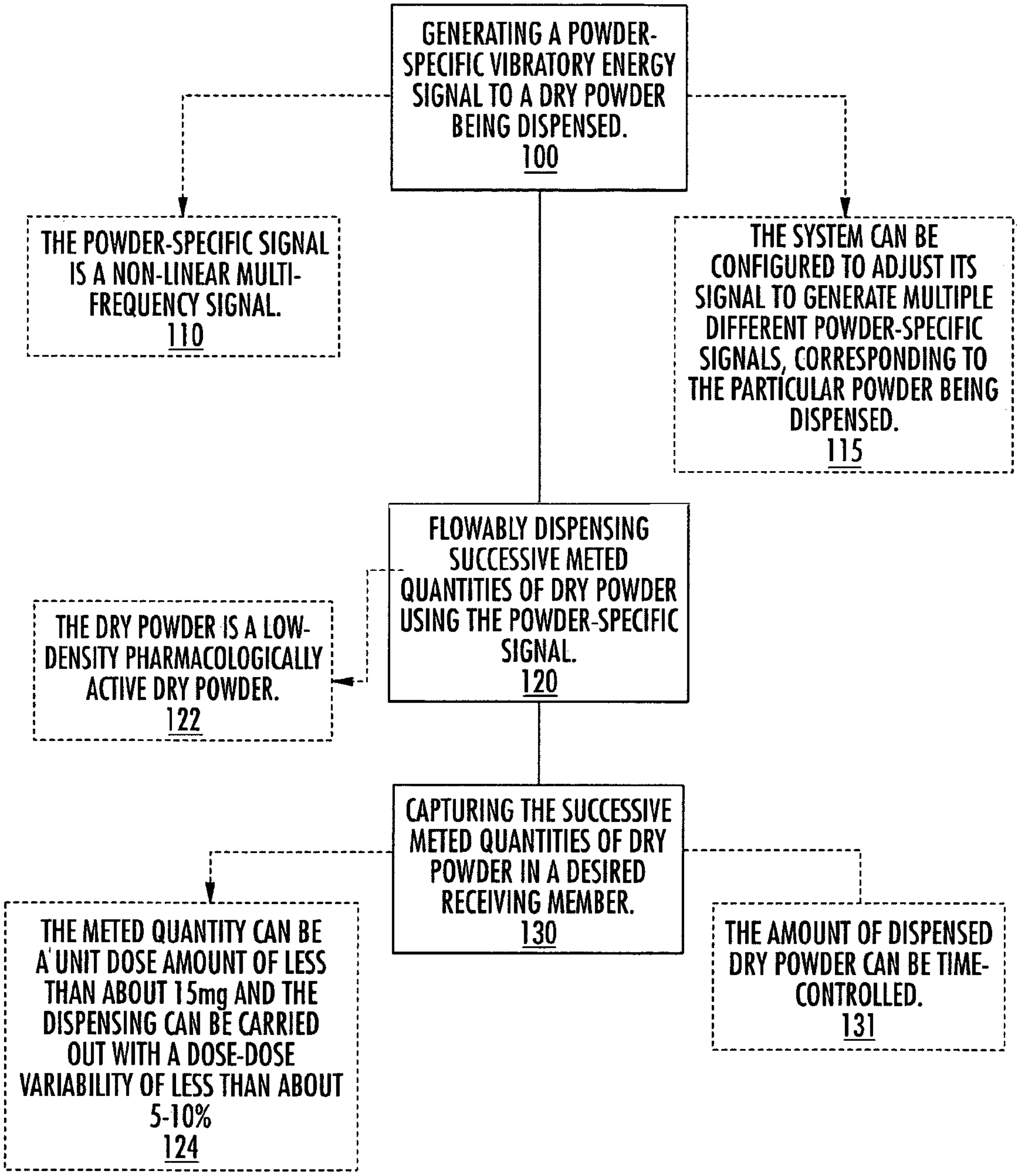

FIG. 1B

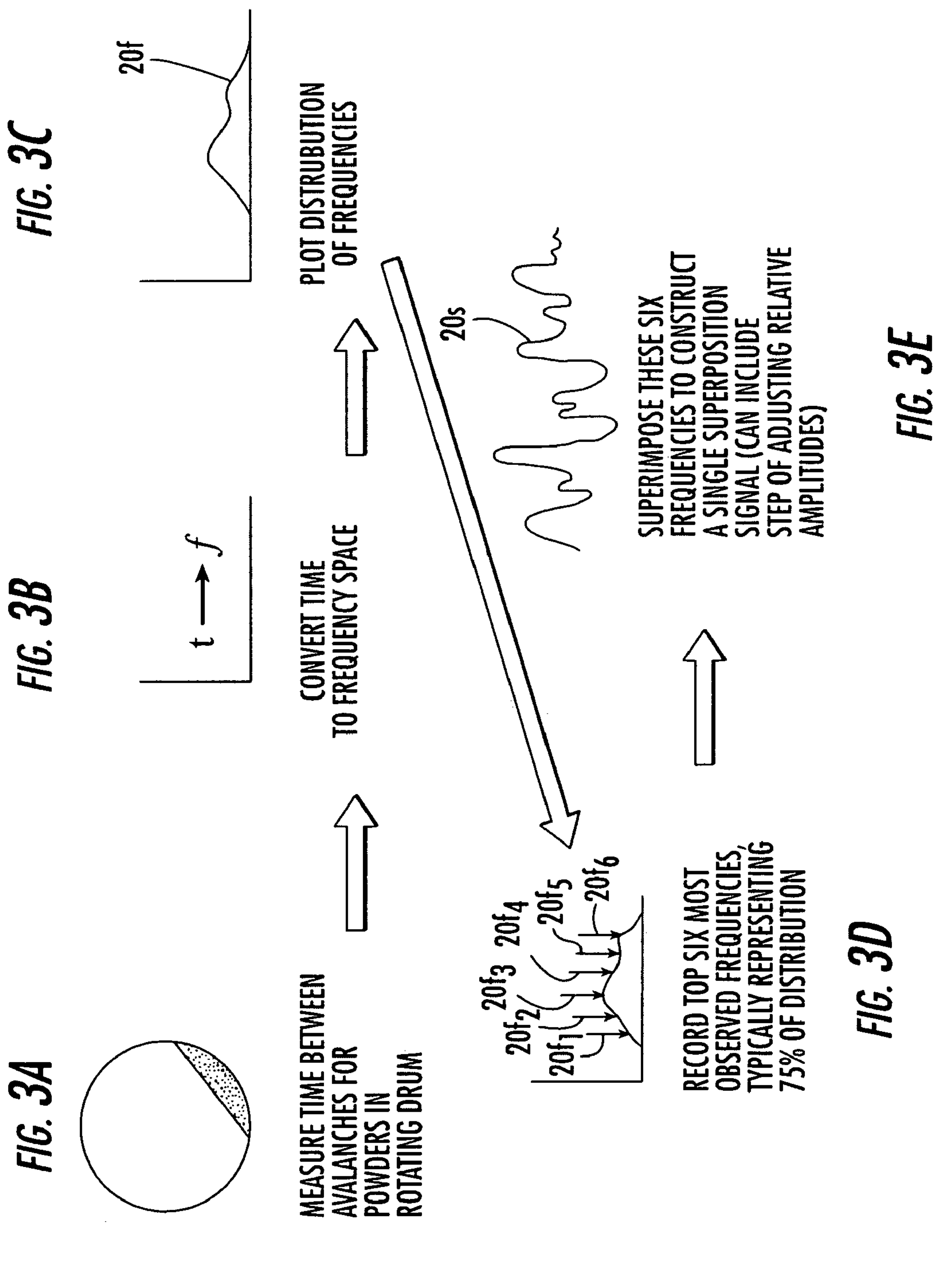
SIGNAL GENERATION ALGORITHM
FIG. 3A
MEASURE TIME BETWEEN AVALANCHES FOR POWDERS IN ROTATING DRUM
FIG. 3B
t → f
CONVERT TIME TO FREQUENCY SPACE
FIG. 3C
20f
PLOT DISTRUBUTION OF FREQUENCIES
FIG. 3D
20f1
20f2
20f3
20f4
20f5
20f6
RECORD TOP SIX MOST OBSERVED FREQUENCIES, TYPICALLY REPRESENTING 75% OF DISTRIBUTION
FIG. 3E
20s
SUPERIMPOSE THESE SIX FREQUENCIES TO CONSTRUCT A SINGLE SUPERPOSITION SIGNAL (CAN INCLUDE STEP OF ADJUSTING RELATIVE AMPLITUDES)

NON-LINEAR VIBRATION / CENTRIFUGATION PRINCIPLE OF POWDER FILLING

BASIC PRINCIPLE:

COMBINE NON-LINEAR FUNCTION WITH CENTRIFUGAL MOTION

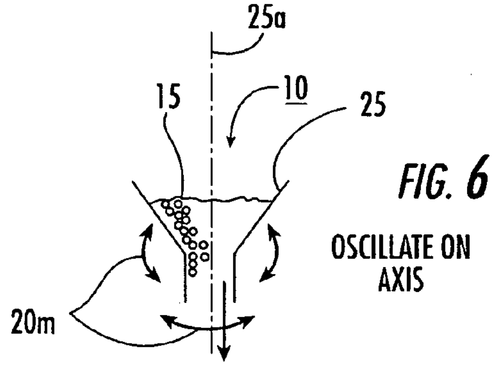

FIG. 6

OSCILLATE ON AXIS

THIS CAN BE ADAPTED TO LOCAL NON-LINEAR VIBRATION.

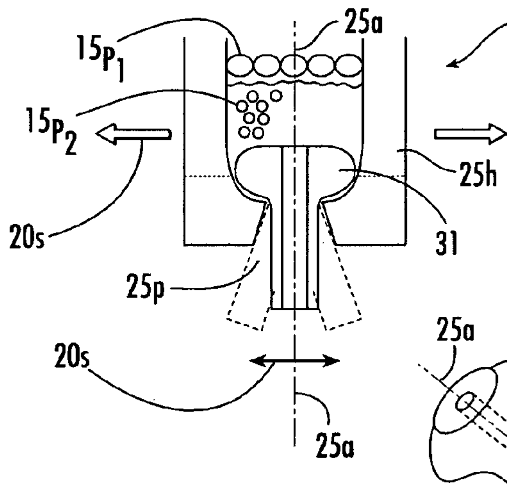

FIG. 7

VIBRATE HEAD

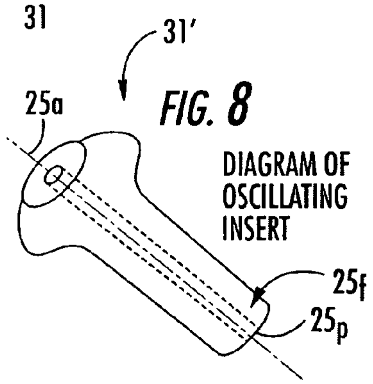

FIG. 8

DIAGRAM OF OSCILLATING INSERT

VIBRATION CAN BE APPLIED TO A RACK OF HEADS FILLING FROM SINGLE HOPPER

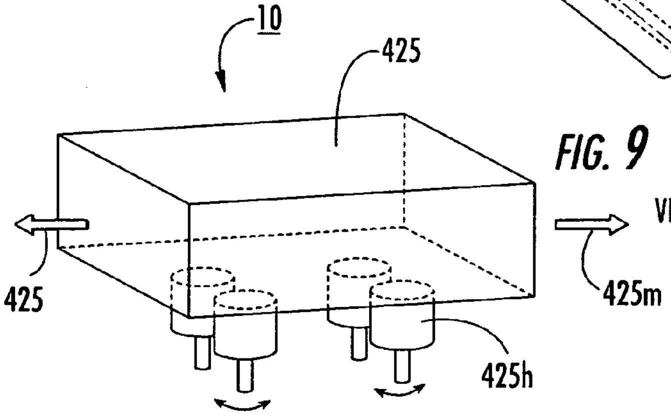

FIG. 9

VIBRATION RACK

RADIUS (OR EXTREMES) OF MOTION CAN BE VERY SMALL. AT HIGH FREQUENCY THE ANGULAR VELOCITY WILL BE SUFFICIENT TO GIVE DIRECTIONAL ACCELERATION TO PARTICLES.

APPARATUS, SYSTEMS AND RELATED METHODS FOR PROCESSING, DISPENSING AND/OR EVALUATINGL DRY POWDERS

RELATED APPLICATIONS

This application is a continuation-in-part of U.S. application Ser. No. 10/434,009, filed May 8, 2003 now U.S. Pat. No. 6,889,690, which claims the benefit of priority to U.S. Provisional Application Ser. No. 60/379,521, filed May 10, 2002, and claims priority to U.S. Provisional Application Ser. No. 60/392,671, filed Jun. 27, 2002, and U.S. Provisional Application Ser. No. 60/440,513, filed Jan. 16, 2003, the contents of the above-referenced applications are hereby incorporated by reference as if recited in full herein.

FIELD OF THE INVENTION

The present invention relates to the processing and/or dispensing of dry powder materials and may be particularly suitable for processing non-pharmaceutical dry powders.

BACKGROUND OF THE INVENTION

In certain industrial applications, the processing and/or handling of dry powders can be problematic. That is, dry powders can have relatively poor flow properties or a tendency to agglomerate, clog output or processing devices, and/or flow in an irregular manner thereby inhibiting uniform flow and/or a desired homogeneity or heterogeneity in resulting target mixtures or applications.

Further, as in pharmaceutical industries, reliable filling, dispensing or outputting precise amounts of dry powders may be difficult. In the past, the metering of dry powder during filling may be provided generally volumetrically, as described in U.S. Pat. Nos. 6,226,962, and 6,357,490. Additional examples of volumetric metering systems are described in U.S. Pat. Nos. 5,865,012 and 6,267,155; these volumetric metering systems propose using an oscillating filling head and/or vibration to aid powder fluidization of pharmaceutically relevant quantities. Others propose injecting a gaseous medium, such as compressed air, to facilitate the filling process, such as described in U.S. Pat. No. 5,727,607. The above-referenced patents are incorporated by reference as if recited in full herein.

Certain dry powder formulations include relatively small particles; these small particles can be subject to forces of agglomeration and/or cohesion (i.e., certain types of dry powders are susceptible to agglomeration, which is typically caused by particles adhering together), which can result in poor flow and non-uniform dispersion, thus inhibiting reliable output. In addition, certain dry powders are hygroscopic in nature, a characteristic that may also inhibit reliable processing. Further, fine or low-density dry powders have a tendency to float or spontaneously aerosolize during dispensing, inhibiting a uniform flow and/or making precision meted or metered dispensing problematic.

Notwithstanding the above, there remains a need to provide improved dry powder processing and/or dispensing systems.

SUMMARY OF THE INVENTION

The present invention provides methods, systems, apparatus and computer program products that can promote a uniform fluid-like flow of one or more dry powders.

In certain embodiments, the operations can employ non-linear vibration input energy that is transmitted to the dry powder during flow. The transmitted energy can be configured or generated so as to flowably output or dispense homogeneous and/or accurate measures of dry powder substances in a manner that inhibits or prevents aggregation, even in mass production environments. In certain embodiments, the non-linear vibration energy is customized and comprises vibration input signals that correspond to selected frequencies associated with a particular formulation undergoing processing to promote uniform dry powder fluid flow (i.e., fluidizing the powder and/or simulating liquid flow characteristics) without aggregation and/or agglomeration. The energy input may be generated by any suitable means including, but not limited to, electrical means, mechanical means, or combinations of same.

The non-linear signal can be determined experimentally using suitable devices. In certain embodiments the device has a floor of a piezoelectric material such as PVDF (known as KYNAR piezo-film or polyvinylidene fluoride) that applies the non-linear signal to the powder while other embodiments employ a rotating drum and evaluate flow characteristics such as time between avalanches (measured in the rotating drum) to select the energy input signal for the powder.

In certain embodiments, the non-linear vibratory input energy comprises a plurality of predetermined frequencies that correspond to selected frequencies associated with flow of the dry powder. The frequencies can be selected experimentally using a flow evaluation apparatus and/or using a property analysis that characterizes certain flow parameters of that particular dry powder being dispensed. Examples of flow analysis parameters (typically from a microflow analysis) include those associated with the dynamic angle of repose or time to avalanche, a fractal analysis of mass flow, or other suitable analysis methodology known to those of skill in the art.

In particular embodiments, to establish the powder-specific energy signals, a Fourier Transform power spectrum and/or phase space complexity analysis of data associated with the angle of repose and/or time to avalanche can be employed. During dispensing, the non-linear vibratory energy may be operated so that multiple frequencies are transmitted concurrently via a single superimposed (weighted) combination of selected frequencies. The transmitted energy signal may be generated as a modulated multi-frequency input signal.

In certain embodiments, the energy input signal can comprise non-linear signals, such as amplitude modulated signals with carrier frequencies in the range of between about 15 kHz to 50 kHz and a plurality of modulation frequencies in the range of between about 10-500 Hz. The systems may be adjustable to generate customized non-linear signals matched to different ones of respective dry powders targeted for processing and/or dispensing to thereby be able to serially dispense and/or mix multiple different types of dry powders using predetermined different energy input signals.

Certain embodiments of the present invention are directed to outputting and/or dispensing dry powder amounts with accuracies of +/−10%, and typically about +/−5% or less variability, and may be carried out with requiring vacuums to dispense the dry powder.

Other embodiments of the present invention are directed to methods and devices for increasing the bulk density without introducing cohesion or aggregation to provide a more stable fluid flow and/or mixing of dry powders such as fine low-density, medium density, and/or high-density dry powders and/or combinations of same.

Certain embodiments of the dispensing systems contemplated by the present invention are directed at increasing the apparent bulk density of the low density dry powder by compressing portions of the powder bed in a dispensing path without evacuating the low-density dry powder material during flow dispensing and without aggregating the particles of the dry powder material.

Particular embodiments are directed to methods of flowably dispensing or processing non-pharmaceutical dry powders from a device having a dry powder flow path. The method includes: (a) generating a first non-linear vibration input signal, the first non-linear input signal comprising a plurality of different selected frequencies that correspond to a first non-pharmaceutical dry powder formulation; and (b) applying the first non-linear vibration input signal to a portion of a dry powder flow path while the first dry powder formulation is flowing therethrough.

The selected frequencies can correspond to flow characteristic frequencies of the first dry powder and the generating step can be carried out to cause the dry powder to flow in a substantially uniform fluidic manner without aggregation and/or agglomeration.

Other embodiments are directed to dry powder processing and/or dispensing systems. The systems include: (a) a device configured to hold a non-pharmaceutical dry powder therein, the device having a dry powder flow path and a wall with an inner surface and outer surface; (b) a quantity of a non-pharmaceutical dry powder disposed in the device; (c) at least one vibration energy generation source operably associated with the device, wherein, in operation, the at least one vibration energy generation source is configured to output a desired non-linear vibratory energy to the dry powder as the dry powder flows through the flow path in the device; and (d) a control module operably associated with the device and the vibration energy generation source. The control module includes: (i) computer program code configured to selectively adjust the output of the vibration energy generation source based on a desired predetermined dry powder specific vibration energy output customized to the non-pharmaceutical dry powder being processed; and (ii) computer program code that directs the vibration energy source to output the selected vibration energy to the device that corresponds to the dry powder in the system.

The computer program code may include a plurality of predetermined different dry powder-specific flow enhancing vibration energy outputs, each associated with a different non-pharmaceutical dry powder and/or dry powder formulation. In particular embodiments, the system may be configured to mix a plurality of different dry powders of different densities to provide a substantially homogeneous mixture.

Other embodiments are directed to computer program products for operating a flowing non-pharmaceutical dry powder processing and/or dispensing system having an associated dry powder flow path with a dispensing port and a vibration energy source associated therewith to facilitate fluidic flow. The computer program product includes a computer readable storage medium having computer readable program code embodied in the medium. The computer-readable program code including: (a) computer readable program code that defines at least one powder-specific non-linear vibration energy signal corresponding to individually predetermined flow property data of the plurality of at least one target dry powder; and (b) computer readable program code that directs the dispensing system to operate using the powder-specific vibration energy signal associated with the target dry powder.

The computer readable program code that defines at least one powder-specific non-linear vibration energy signal can comprise computer program code the defines a plurality of different non-linear input signals, a respective one for each of a plurality of different dry powders, each of the vibration energy signals based on individually determined flow property data.

Still other embodiments are directed to apparatus for processing, dispensing and/or expelling non-pharmaceutical dry powders. The apparatus includes: (a) an elongate flow channel having a width, length, and depth, the flow channel having axially spaced apart inlet and outlet ports, wherein the elongate flow channel is configured to extend in an angular orientation of between about 10-75 degrees relative to the axial direction of flow; (b) a flexible piezoelectric layer configured to overlie the flow channel so that, in operation, the piezoelectric layer is able to flex upwardly away from the lowermost portion of the underlying flow channel; (c) a quantity of non-pharmaceutical dry powder positioned in the flow channel; and (d) a signal generator operatively associated with the piezoelectric layer, wherein, in operation, the signal generator is configured to output a signal for flexing the piezoelectric layer which vibrates the dry powder in the elongate flow channel.

Other embodiments are directed to methods for selecting and/or determining customizable excitation signals for processing and/or dispensing non-pharmaceutical dry powders. The methods include: (a) providing an elongate flow channel having a floor of piezoelectric material; (b) selecting an angle of orientation for the flow channel such that the flow channel angularly extends in a non-vertical, non-horizontal orientation in the axial direction; (c) providing a quantity of a target non-pharmaceutical dry powder; (d) outputting a vibration excitation signal having a first carrier frequency from a signal generator to the piezoelectric material; (e) flowing the dry powder out of the flow channel; (f) outputting a vibration excitation signal having a second carrier frequency from the signal generator to the piezoelectric material; and (g) determining the vibration signal for the target non-pharmaceutical dry powder that generates a uniform fluid-like substantially non-agglomerated flow.

Still other embodiments are directed to methods of processing and/or dispensing a non-pharmaceutical dry powder. The methods include: (a) providing an elongate flow channel having a powder support floor formed of a flexible piezoelectric material and inlet and outlet ports; (b) directing a quantity of non-pharmaceutical dry powder into the inlet port of the elongate flow channel; (c) vibrating the piezoelectric material with a non-linear electric excitation signal so that the piezoelectric material deflects upwardly; and (d) flowing the dry powder out of the outlet port responsive to the vibrating step.

The method may optionally include adjusting the orientation angle of the elongate floor channel so that the flow channel angularly extends in a non-vertical, non-horizontal configuration and so that the outlet port is lower than the inlet port. The non-linear excitation signal may be formed using a plurality of superpositioned modulating frequencies.

Embodiments can be configured to provide, mix and/or dispense a plurality of different dry powders separately or concurrently.

The present invention contemplates providing systems similar to the methods, and certain systems can be described by inserting "means for" in front of the operations noted under any of the methods described above. These and other objects and/or aspects of the present invention are explained in detail in the specification set forth below.

BRIEF DESCRIPTION OF THE DRAWINGS

FIG. 1B is a flow diagram of examples of operations that can be used to carry out embodiments of the invention.

FIGS. 3A-3E illustrate a series of operations that can be carried out to determine a suitable signal according to embodiments of the present invention.

FIG. 6 is a schematic front section view of a dispensing system according to additional embodiments of the present invention.

FIG. 7 is a schematic front partial section view of another embodiment of the present invention.

FIG. 8 is a side perspective view of an oscillating insert member according to embodiments of the present invention.

FIG. 9 is a schematic front perspective view of a dispensing system according to additional embodiments of the present invention.

DESCRIPTION OF EMBODIMENTS OF THE INVENTION

Figure 1A:
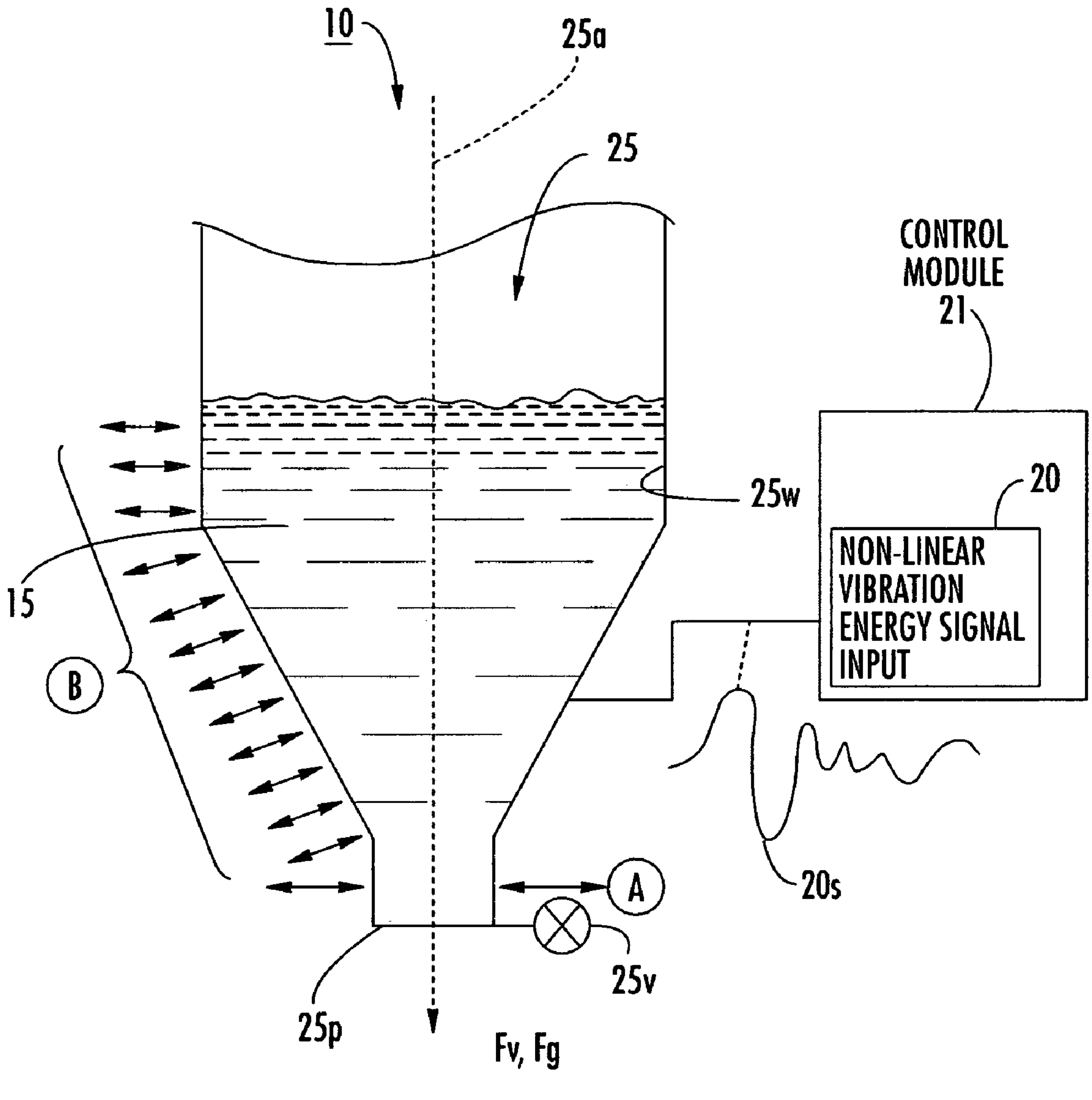
FIG. 1A is a schematic enlarged partial front view of a filling or dispensing nozzle according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations, unless specified otherwise.

The term "meted" is used interchangeably with the term "metered." In addition, the sequence of operations (or steps) is not limited to the order presented in the claims unless specifically indicated otherwise. Where used, the terms "attached", "connected", "contacting", and the like, can mean either directly or indirectly, unless stated otherwise. Further, the term "hopper" is broadly used for ease of description to designate devices, a transient portion or holding portion of the flow path in a dispensing system and can include, but are not limited to, a dispensing head(s) or nozzle(s), a portion of a flow path, and/or a reservoir body, and the like. The figures are not necessarily shown to scale.

In the description of the present invention that follows, certain terms are employed to refer to the positional relationship of certain structures relative to other structures. As used herein, the terms "front" or "forward" and derivatives thereof refer to the general or primary direction that the dry powder travels as it is dispensed; these terms are intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the directions opposite, respectively, the forward and downstream directions.

As used herein, the term "non-linear" means that the applied vibratory action or input signal has an irregular signal shape and/or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input operates without a fixed single or steady state repeating amplitude at a fixed frequency or cycle. This non-linear vibratory input can, thus, transmit a variable amplitude motion to the dry powder (as either a one, two and/or three-dimensional vibratory motion). In the past, other attempts for fluidization may have used either airflow or vibration with linear frequencies that may cause aggregation. For example, in the past, others have proposed uniform frequency systems (using vibrating orifices, ultrasonic systems, and the like) to generate sinusoidal, square, or other uniform signals.

Embodiments of the invention may be particularly suitable for dispensing low-density dry powders. However, other embodiments are directed to processing unit density, medium-density and/or high-density dry powders. The term "low-density dry powder" means dry powders having a density of about 0.8 g/cm$^3$ or less. In particular embodiments, the low-density powder may have a density of about 0.5 g/cm$^3$ or less. The term "unit density dry powder" means dry powders having a density of about 1 g/cm$^3$. The term "medium density dry powder" means dry powders having a density greater than 0.8 g/cm$^3$ and less than or equal to about 1.2 g/cm$^3$, and the term "high density dry powders means dry powders having a density greater than 1.2 g/cm$^3$. Certain embodiments are directed to be able to mix, handle or process a plurality of different dry powders, such as two or more combinations of low, high and/or medium dry powders.

Embodiments of the invention may be used to process dry powder formulations having particulates which have particle sizes that on average are less than about 50 μm, and typically in the range of about 0.5-50 μm. In certain embodiments, the dry powder formulations have particle sizes in the range of about 0.5 μm-20.0 μm, and more preferably in the range of about 0.5 μm-8.0 μm. Other embodiments may be used to process dry powders having particulates that have, on average, particle sizes above 50 μm.

The dry powder formulation can be dispensed alone or also be dispensed to include flow-enhancing ingredients, which typically have particulate sizes that may be larger than the active ingredient particulate sizes. In certain embodiments, the flow-enhancing ingredients can include excipients or constituents that have particulate sizes on the order of about 50-100 μm or greater.

In certain embodiments, the dry powder may be formulated with an increase in concentration (an increased percentage of active dry powder constituents rather than the flow enhancing constituents) over conventional blends.

Certain embodiments of the present invention are directed for use with non-pharmaceutical dry powders. As used herein, the term "non-pharmaceutical" means non-FDA (United States Food and Drug Administration or similar foreign regulatory body) regulated substances that are non-drug and/or (non-oral or inhalant) non-therapeutic or non-diagnostic dry powders, such as powders used in non-medical (typically commercial) industrial, laboratory, and/or research applications: the term "non-pharmaceutical" includes dry powders used in coating applications for medical use (such as coatings on and/or in medical devices which may provide bioactive constituents).

Examples of non-pharmaceutical applications may include dry powder applications that desire one or more of: low dust production environments, uniform and/or homogeneous mixtures (such as uniform powder density within a mixture of several constituent powders), reliable and/or precision (even at relatively small quantities) dispensing capacity, and clog resistant filling or processing systems. In particular embodiments, the non-linear signals of the present invention may be used for non-pharmaceutical dry powders such as, but not limited to, toners, inks, dyes, chemicals, explosives, munitions, cosmetics, precious metals (titanium, platinum, gold, silver and the like), powder coatings (such as in spray coating techniques in consumer, automotive and/or medical device manufacturing industries), powder metal precursors, nanoparticle dry powder delivery, metal injection molding, powder metallurgy, dry powder food materials (spices, additives, etc.) and applications where it is desirable to reduce and/or eliminate the amount of conventional additives (lubricants and/or excipients) added to dry powders to facilitate flowability (to potentially provide material and/or labor or other cost savings).

Certain particular embodiments of the present invention may be suitable for use in metal powder processing for relatively dense powders such as high-density metal powders (such as tungsten-carbide and ti-carbide) because metal powders can have a tendency to settle and/or agglomerate. In other embodiments, the non-linear signal can be applied to a spray application process such as a spray gun nozzle and/or other portion of the flow path to reduce clogging and/or provide a relatively reliable and constant output flow of the dry powder during operation.

Other embodiments of the present invention may be useful for providing improved mixing capability to mix at least one dry powder in an industrial (non-pharmaceutical) application using a non-linear signal to provide improved mixture homogeneity. Examples of non-linear signals will be described further below.

Turning now to FIG. 1A, a portion of a dispensing system 10 is shown. The system 10 comprises a dispensing hopper 25 with a dispensing port 25*p*. A quantity of a dry powder 15 can be disposed in the hopper 25 for dispensing. As used herein, the term "dry powder" is used interchangeably with "dry powder formulation" and means the dry powder can comprise one or a plurality of constituents or ingredients with one or a plurality of (average) particulate size ranges. The dry powder may be a dry powder with cohesive or agglomeration tendencies. As is also shown, the dispensing system 10 also comprises a non-linear signal generator 20 that is operably associated with the hopper 25. The non-linear signal generator 20 is configured to generate a vibratory signal 20*s* that facilitates the flowable dispensing of the dry powder 15. The hopper 25 and port 25*p* define a flow path for the dry powder 15. An axis 25*a* extends vertically axially through the port and hopper, 25*p*, 25, respectively. The system 10 may include a valve 25*v* operably associated with the port 25*p* to controllably and/or selectively open and close the port 25*p* (and, thus, the dry powder flow path) during operation.

As shown, the signal generator 20 may be operably associated with a control module 21. The signal generator 20 may be configured to transmit the vibratory energy either locally to a limited site (shown as position "A" with lateral arrows representing lateral movement) or distributed along a major portion of the length of the hopper 25 (shown by space "B" with a plurality of distributed arrows along a portion of the wall 25*w* of the hopper 25).

In particular embodiments, the signal generator 20 can include a transducer that is driven by an amplifier to provide the vibratory input. The transducer can be driven to have relatively small amplitude output such as about 100 mm or less, typically less than 10 mm, and in certain embodiments, about 1 mm or less. In other embodiments, the signal generator 20 can be configured to force the hopper or other portion of the flow path (whether wall, outer perimeter of the device itself or other component which transmits the vibratory energy to the dry powder) to move, deflect and/or vibrate with relatively small amplitudes of less than about 1 mm. In certain embodiments of systems that employ at least one transducer, the transducer may be driven with low energy such as less than about 100 mW.

FIG. 1B illustrates examples of operations that may be used to dispense dry powder according to embodiments of the present invention. A powder-specific dry powder vibratory energy signal can be generated (block 100) (corresponding to the particular dry powder being currently dispensed). The system can be configured to generate multiple different signals (block 115), and, as such, the signal generator can be selectively adjusted to output the particular signal corresponding to the dry powder (or dry powder mixture) then being dispensed or processed. The powder specific vibratory signal may be a non-linear signal comprising a plurality of selected frequencies (block 110). The non-linear signal can fluidize the powder in such a way that a powder "flow resonance" is generated allowing precision flowable dispensing and/or reducing, inhibiting and/or preventing agglomeration.

In particular embodiments, the signal can be configured to generate a downwardly oriented force vector on the dry powder during flow that can increase the apparent bulk density of the dry powder to simulate and/or cause the dry powder to flow in a substantially uniform fluid-like manner. In particular embodiments, the dry powder can comprise a metallic dry powder such as a precious metal or metal powder and/or metal powder precursor (block 122). Other embodiments contemplate processing and/or dispensing alternative dry powders, such as, by way of example, those described above.

Again referring to FIG. 1B, the dry powder can be flowably output from a device or along a flow stream using the powder-specific signal (block 120). In certain embodiments, successive meted quantities of dry powder can be dispensed using the corresponding powder-specific signal (block 130). In particular embodiments, the amount of dispensed dry powder may be output based on a time-controlled input to the signal generator and/or valve (block 131) rather than requiring volumetric dispensing as with conventional protocols.

The output quantities of dry powder can be successively captured in a desired receiving member(s). The vibratory signal may be a low energy signal.

The powder can be dispensed into suitable receiving members, whether bulk reservoirs or mold cavities, unit packages, and the like. The meted quantity can be amounts of less than about 15 mg, with variability of less than about 5-10%.

Figure 1C:
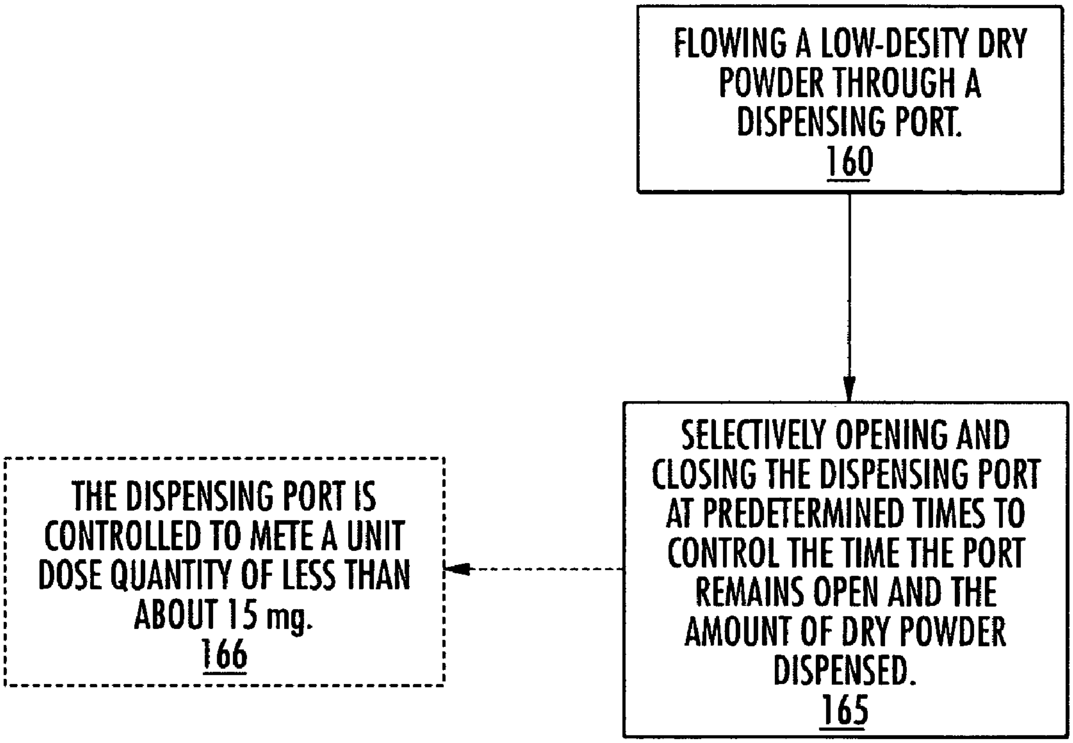
FIG. 1C is a flow diagram of examples of operations that can be used to mete amounts of dry powder according to embodiments of the present invention.

FIG. 1C illustrates one method of controllably filling meted amounts of low-density dry powder. The dry powder flows through a dispensing port (block 160) and the dispensing port is selectively opened and closed at predetermined times to control the amount of time the flow path is open and, thus, the amount of dry powder dispensed (block 165). The dispensing port may be configured to yield unit amounts of less than about 15 mg (block 166). The time-controlled dispensing port may be operated to yield precision-meted amounts of dry powder under about 10 mg. The term "precision" means less than about a 5% variation from a planned amount, and/or between meted unit amounts, and may provide less than about a 2% variation in certain embodiments.

The dispensing head may be held in a static position with respect to an underlying dispensing location. As such, the underlying receiving member may be on a moving surface (such as a conveyor with a controlled conveyor speed) that causes a different receiving member or location to be placed under the dispensing port at each open interval for successive automated filling. In other embodiments, the dispensing port can be placed on a moveable head with the receiving member(s) static, and the head can be translated to overlie different receiving regions at different dispensing times. In yet other embodiments, the dispensing port or nozzle may be moveable as well as the target receiving member.

Figure 2A:
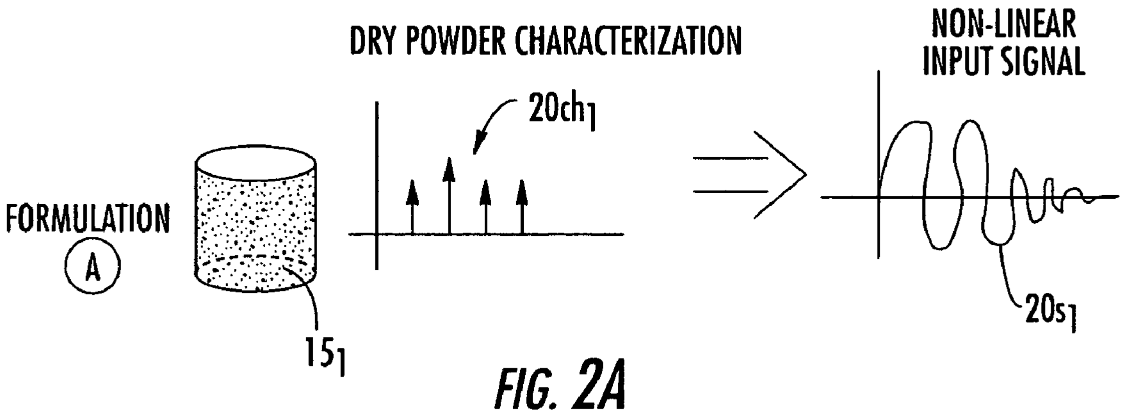
FIGS. 2A-2C is a schematic illustration of the characterization and generation of customized energy input signals for different dry powders according to embodiments of the present invention.
Figure 2B:
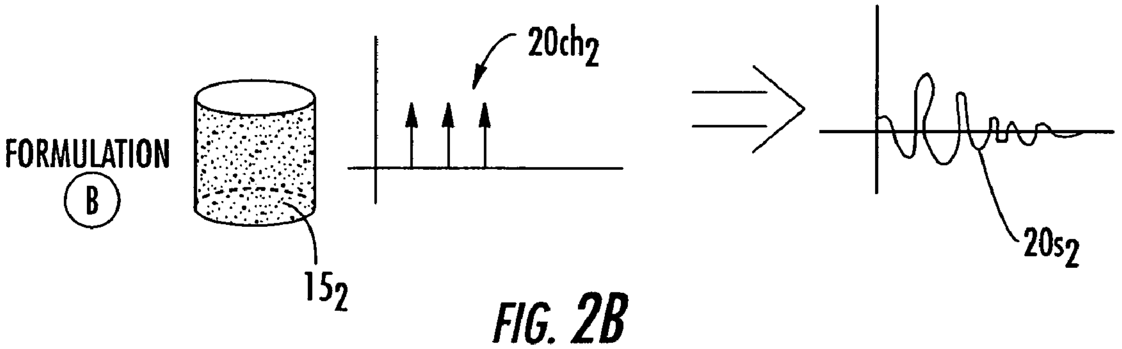
Figure 2C:
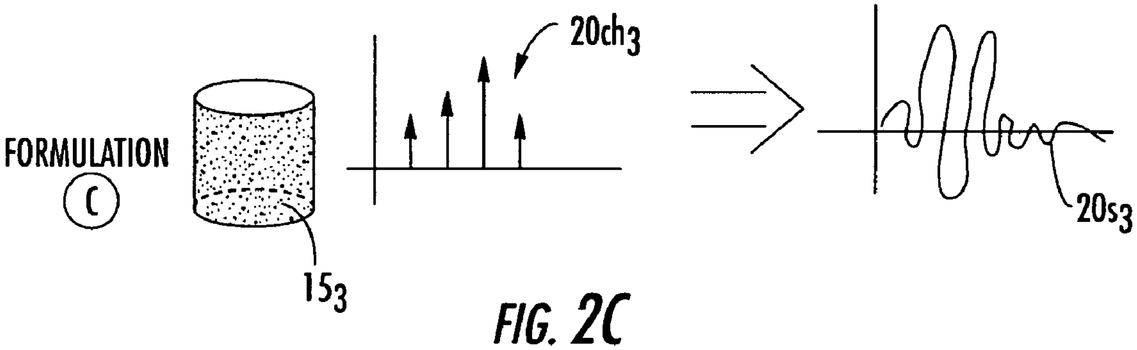

FIGS. 2A-2C illustrate three different dry powders $\mathbf{15}_1$, $\mathbf{15}_2$, $\mathbf{15}_3$, each of which can be analyzed and/or characterized ($\mathbf{20}ch_1$, $\mathbf{20}ch_2$, $\mathbf{20}ch_3$, respectively). Custom or corresponding individual (non-linear) input signals with frequencies selected from the corresponding characterization that are specifically targeted to that dry powder to facilitate fluidic flow during dispensing can be determined for each dry powder $\mathbf{15}_1$, $\mathbf{15}_2$, $\mathbf{15}_3$. The simulated powder-specific signals are shown by the signals $\mathbf{20}s_1$-$\mathbf{20}s_3$.

The signal generator 20 (FIG. 1A) may be programmed with a plurality of predetermined different signals 20*s*, or if a manufacturing apparatus dispenses only a single dry powder, the signal generator 20 may be programmed with a single signal 20*s*. Appropriate powder-specific signals can be determined experimentally and/or computationally at an OEM or evaluation site and forwarded to be input onto dispensing systems at selective use sites (via computer program code that direct the generation of the dry powder flow promoter signal).

FIGS. 3A-3E illustrate an example of operations that may be carried out to generate a dry powder-specific signal. A microflow analysis of the dry powder to be dispensed can be performed to assess avalanching flow profiles and/or other suitable mass/time flow profiles. The analysis can be carried out to select predominant oscillatory frequencies for a particular dry powder that, when applied to the powder during flowable dispensing, can promote uniform mass flow.

Methods and devices for analyzing rapid powder flow measurement are described in Crowder et al., *Signal Processing and Analysis Applied to Powder Behavior in a Rotating Drum,* Part. Part. Syst, Charact. 16, 191-196 (1999); Crowder et al, *An instrument for rapid powder flow measurement and temporal fractal analysis,* Part Syst Charact 16, pp. 32-34, (1999); and Morales-Gamboa, et al., *Two dimensional avalanches as stochastic Markov processes,* Phys Rev. E, 47 R2229-2232 (1993), the contents of which are hereby incorporated by reference as if recited in full herein. See also, Ditto et al., *Experimental control of chaos,* Phys. Rev. Lett., 65: 3211-3214 (1990); B. H. Kaye, *Characterizing the Flow of Metal and Ceramic Powders Using the Concepts of Fractal Geometry and Chaos Theory to Interpret the Avalanching Behaviour of a Powder,* in T. P. Battle, H. Henein (eds.), *Processing and Handling of Powders and Dusts, The Materials and Metals Society,* 1997; B. H. Kaye, J. Gratton-Liimatainen, and N. Faddis. *Studying the Avalanching Behaviour of a Powder in a Rotating Disc.,* Part. Part. Syst. Charact. 12:232-236 (1995), and Ott et al., *Controlling Chaos,* Phys. Rev. Lett. 64: 1196-1199 (1990), the contents of each of these articles are also incorporated by reference as if recited in full herein. Using the principals and relationships described in one or more of these articles with signals derived from analyses of mass flow and/or microflow, one can determine custom powder specific signals that may be able to achieve uniformly flowing dry powders.

As shown in FIG. 3A, the time between avalanches, for a particular dry powder of interest, may be evaluated experimentally using a rotating drum. This time information may be converted to frequency space (frequency domain) as shown in FIG. 3B. FIG. 3C illustrates that a distribution of frequencies 20*f* can be determined (computationally or via computer models). Then, a desired number of selected frequencies can be identified. The frequencies selected may span a desired statistically significant percentage of the distribution or be the frequencies most observed in the analysis spectrum. The term "most observed" means those frequencies occurring the greatest number of times in the distribution. For example, the number of different frequencies selected may be at least the three most observed different frequencies and/or sufficient frequencies to represent at least about 50% of the distribution. In certain embodiments, the number can be at least about 5, and typically about 6, or a number sufficient to represent at least about 75% of the frequency distribution. To select the number, two or three of the most observed frequencies can be used to form the vibration signal. The results can be analyzed experimentally and additional frequencies may be added to the combined non-linear signal to improve fluidic flow performance.

FIG. 3D illustrates that six of the most observed frequencies 20*f*$_1$-20*f*$_6$, in the distribution plot 20*f* can be selected. FIG. 3E illustrates that the selected frequencies can be superimposed to generate a single superposition signal (that may also include weighted amplitudes for certain of the selected frequencies or adjustments of relative amplitudes according to the observed frequency distribution). Thus, FIG. 3E illustrates a derived non-linear oscillatory or vibratory energy signal that may be used to dispense a particular dry powder.

Referring again to FIG. 3D, the signal can be created digitally by computer code means employing mathematical or numerical computation techniques and relevant equations. For example, for a signal 20*s* having representative frequencies "$f_{1-n}$," the cumulative signal $x_{signal}$ (20*s*, FIG. 3D) can be generated include a plurality of signal components, $xf_1$-$xf_n$ (shown as 20*f*$_1$-20*f*$_n$, in FIG. 3D) at each desired frequency, $f_n$, each component having an amplitude "a" at its frequency as described below. Using the spectrum shown in FIG. 3D noting that the most observed frequency in FIG. 3D is 20*f*$_3$, the following equations may be used to generate the non-linear signal.

For an index, "n" ranging from 0-15,999, used to generate the digital signal:

$$n=[0:15999] \quad \text{Equation (1)}$$

$$xf_3=\sin(2\pi n/16000) \quad \text{Equation (2)}$$

$$xf_2=af_2\sin(2\pi n(f_2)/16000(f_3)) \quad \text{Equation (3)}$$

$$xf_4=af_4\sin(2\pi n(f_4)/16000(f_3)) \quad \text{Equation (4)}$$

This evaluation can be continued for a desired number of frequencies to render a representation of a sufficient number of frequencies/spanning a sufficient portion of the spectrum. The powder-specific, non-linear signal can be generated by summing the selected individual frequency components.

$$x_{signal}=xf_3+xf_4+xf_4 \quad \text{Equation (5)}$$

In certain embodiments, the overall power in the signal, $x_{signal}$, can be increased by adding a phase shift to one or more of the summed components. For example, for component $xf_2$, the associated signal contribution can be adjusted by the following equation:

$$xf_2=af_2\sin(2\pi n(f_2)/16000(f_3)+m\pi/n_f) \quad \text{Equation (6)}$$

Where "m" is the number at this frequency and $n_f$ is the total number of frequencies contained in the signal.

Figure 4:
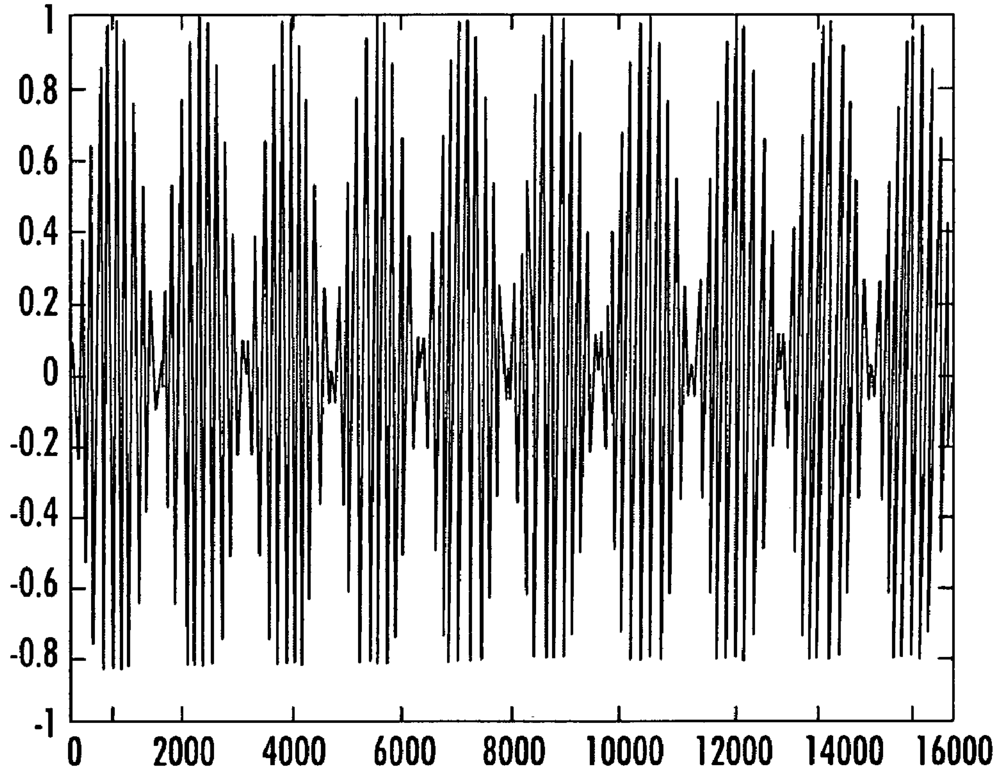
FIG. 4 is a graph of the vibration amplitude as a function of frequency used to disperse the dry powder used to vibrate the powder during filling according to embodiments of the present invention.

FIG. 4 illustrates an example of an amplitude-modified vibratory signal of a dry powder that can include a kHz carrier frequency (such as between about 5 kHz-50 kHz) modified by low modulating frequencies (typically between about 10-200 Hz) that may be generated by certain embodiments of the present invention. The vibration signal may include a plurality of frequencies (applied serially or concurrently in a superimposed manner) that are selectively applied to the dry powder formulation flowing through a hopper and/or nozzle so that it is modified to match or correspond to the flow characteristics of the dry powder formulation to reliably induce a fluid flow state to promote uniform non-aggregated flow.

An example of a commercially available rotating drum is the TSI Amherst Aero-Flow™ (TSI Inc. Particle Instruments/Amherst, Amherst, Mass.). This device provides powder flow information by detecting the occurrence of and recording the time between avalanches. The Aero-Flow™ has been utilized to demonstrate correlation between powder flow and tableting performance for like materials. The instrument uses a photocell detector for its avalanche detection mechanism. A light shines through the Plexiglas drum and is obscured from the detector to varying degrees by powder contained in the drum. As the drum rotates, the powder heap rises with the rotation and the photocell detector is uncovered. When an avalanche occurs in the powder heap, the light is again blocked by the cascading powder. The change in light intensity striking the photocell is interpreted by the data collection software as the occurrence of an avalanche. In other embodiments, the powder can be evaluated to determine and/or measure avalanches using a sensitive microphone/accelerometer that can be mounted on the rotating drum. Avalanches can be determined acoustically from the sound generated by the avalanching powder. This evaluation technique may allow for reduced amounts of the dry powder that is desired for use during the avalanche evaluation to milligram quantities, such as about 10 mg or less. In any event, statistics of the time between avalanches can be determined and an avalanche time phase space plot can be generated.

A useful method of presenting data to discover the dynamics of a system is the Poincaré phase space plot. This phase space approach is one in which variables sufficient to describe a system are contained in a single vector. The state of the n variables at an instant in time is a point in phase space. Plotting the time evolution of the system in phase space can map its dynamics. As an example, a simple harmonic oscillator can be pictured in phase space by plotting the position versus the velocity, variables that completely describe the system. The phase space plot of the harmonic oscillator is a circle reflecting the periodic, but 90-degrees out of phase, exchange of maximum position and velocity. A damped harmonic oscillator would appear as a simple attractor with the trajectory encircling and eventually collapsing to the origin as the position and velocity reach zero. The correlation dimension provides a measure of the space filling properties of the phase space representation. A hypersphere of dimension D and radius r is centered on each data point. The number of data points falling within that sphere as a function of the radius may be displayed in a log-log plot. The slope of the resulting line may be termed the correlation dimension.

To determine an appropriate vibration signal, a suitably sized dry powder sample can be disposed in the drum (such as about 60 ml of powder). The drum can be allowed to rotate through a single revolution before data collection begins so that initial conditions over several powders are similar. The drum can be rotated at 0.5 revolutions per minute for 6 minutes. The photocell voltage signal can be sampled at 25 Hz using a PC based data acquisition board (DI-170, Dataq Instruments, Akron Ohio). Time between avalanches and the voltage change upon avalanching can be acquired from the voltage signal. A video camera can be situated perpendicular to the drum can record the powder as it rotates in the drum. A grid can be placed behind the drum, without obscuring the photocell, to facilitate determination of the angle of the powder relative to the horizontal. Upon viewing the video, the base and height of the powder heap can be recorded and the angle can be determined using the trigonometric relation, θ=arc tan(height/base). Determinations of the instantaneous powder angle can be performed at 200 millisecond intervals. This rate corresponds to every sixth frame of the video, determined previously by recording the counting of a stopwatch.

Angle data time series can comprise at least about 500 data points or 100 seconds. Computation of a Fourier power spectrum can be performed using the Welch method with a 128 point Kaiser window and zero padding to 1024 data points for the FFT calculation. Other suitable methods can be employed as is known to those of skill in the art.

The avalanche statistics can be presented in terms of the mean and standard deviation of time between avalanches. A phase space plot can be generated by plotting the $n^{th}$ time to avalanche against the $(n-1)^{th}$ time to avalanche. For the angle of repose, phase space plots consist of the instantaneous deviation from the mean angle versus the first time derivative of the angle. The rate of change of the angle at each data point can be approximated from the preceding and subsequent data points using Newton's method.

The uniformity of flow can be discerned by examining the frequency and the amplitude of the oscillations. Certain dry powder signals may exhibit a higher degree of variability in frequency and in amplitude relative to others. By use of the Fourier transform (FT) power spectrum, energy distributions can be obtained. Energy spectrums that are dispersed over a range of frequencies can indicate more irregular flow. The mean time to avalanche can be subtracted from the instantaneous time to avalanche to deconvolute relevant frequency data in angle phase space plots. Identifying the predominant frequencies and selectively combining and/or using those identified frequencies as the basis of the transmitted vibration energy excitation signal may induce resonance in the dry powder during dispensing.

Figure 13:
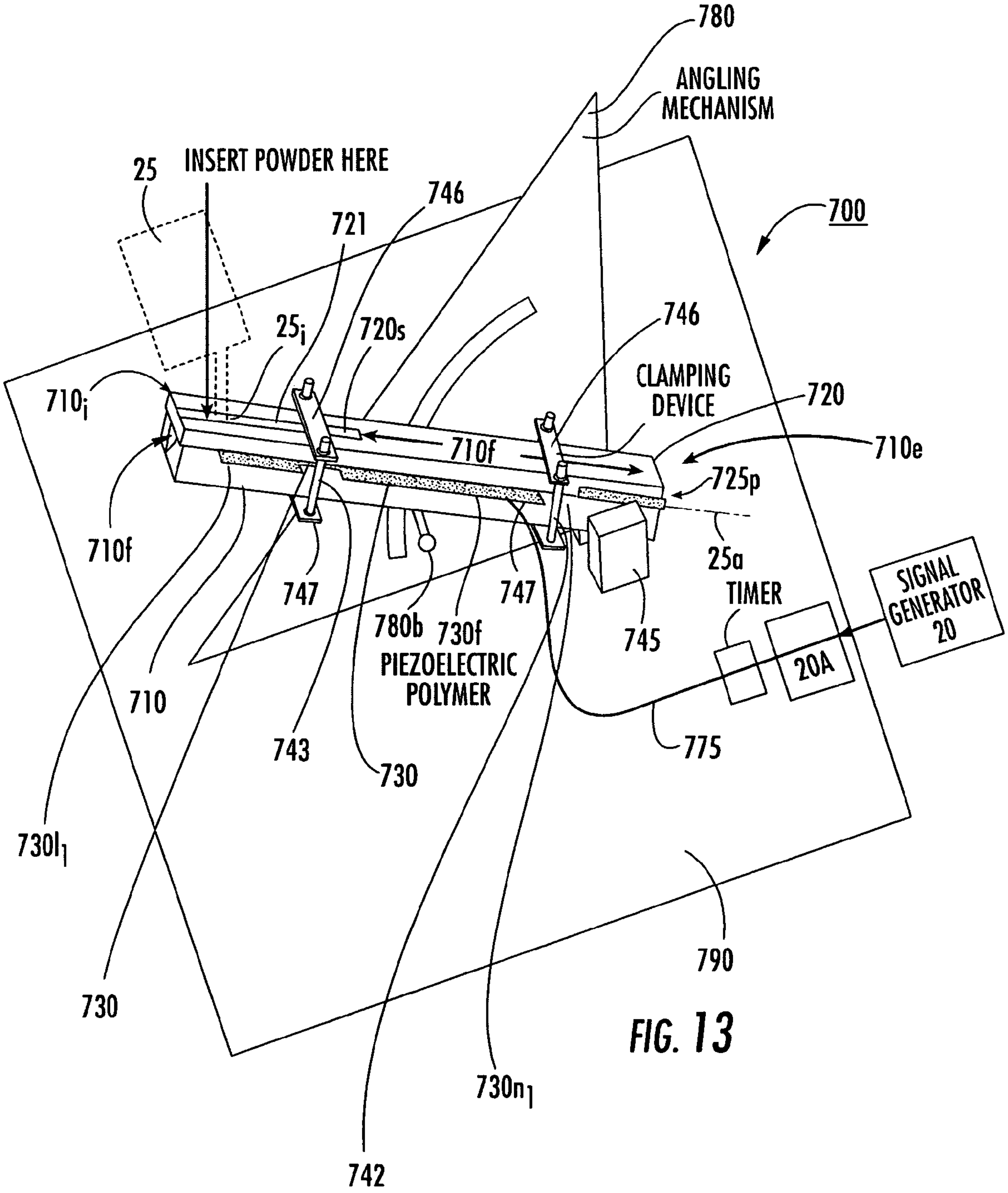
FIG. 13 is a perspective view of a dispensing mechanism according to embodiments of the present invention.

Other analysis methods and apparatus can be employed. For example, as shown in FIG. 13, an example of one apparatus that is configured to allow adjustment of the excitation signal and/or angle of flow for a powder under evaluation, can be used and the adjustments altered until reliable fluidic flow is output. The operational parameters determined in that manner can be used to define the non-linear customized fluidic flow signal for dispensing that powder. The apparatus shown in FIG. 13 may also be used during active dispensing using one or more of the devices (depending on the desired delivery capacity). This apparatus will be discussed further below.

Referring back to FIG. 1A, the vibratory energy signal 20*s* can be generated and applied to the dry powder 15 so that the dry powder is exposed to a force vector having a downward orientation Fv as it travels through a portion of the hopper 25 and exits the dispensing port 25*p* (in the same direction as Fg). During dispensing, the apparent bulk density of the dry powder can be temporarily increased over its real bulk density without (irreversibly) aggregating the dry powder thereby allowing the dry powder to flow in a more uniform fluid like manner. The non-linear vibration energy signal may be supplemented by other vibration energies as will be discussed further below.

In certain embodiments, the signal 20*s* and/or the vibration of the energy transmitting surfaces in the channel 25 may concurrently or successively rapidly vibrate the dry powder at a plurality of different frequencies (at similar or different amplitudes) in the range of between about 10 Hz-1000 kHz. In certain embodiments, the frequencies are between about 10-200 Hz, such as 10-60 Hz. In other embodiments, they may be in the range of between about 7 kHz-100 kHz, such as 7.5 kHz or more such as frequencies between about 15 kHz to 50 kHz.

The vibration signal 20*s* can be generated by any suitable vibratory source, including electrical means, mechanical means, and/or electromechanical means. That is, at least a portion of the hopper 25 can be (physically) translated by and/or in a predetermined non-linear vibration imparting motion to impart a downwardly oriented force vector Fv using powder specific signals. Examples of vibratory sources include, but are not limited to, one or more of: (a) ultrasound or other acoustic or sound based sources (above, below or at audible wavelengths) that can be used to instantaneously apply non-linear pressure signals onto the dry powder 15; (b) electrical or mechanical deflection of the sidewalls of the hopper or dispensing port 25*p*; (c) movement of the hopper 25 or portions thereof (such as, but not limited to, physically moving and/or deflecting portions such as solenoids, piezoelectrically active portions and the like) non-linearly about the axis 25*a* (comprising one or more of selectably controllable amounts of travel in the horizontal, vertical, and/or diagonal directions relative to the flow path axis 25*a*); and (d) oscillating or pulsed gas (airstreams), which can introduce changes in one or more of volume flow, linear velocity, and/or pressure. Examples of mechanical and/or electromechanical vibratory devices are described in U.S. Pat. Nos. 5,727,607, 5,909,829 and 5,947,169, the contents of which are incorporated by reference as if recited in full herein.

Referring again to FIG. 1C, in certain embodiments, at least a portion of the length of the hopper walls 25*w* (either an inner, outer or intermediate surface) may be formed of a piezoelectrically active material so that application of a (non-linear) powder specific voltage signal generates (non-linear) flexure of the wall 25*w* which can be transmitted to the dry powder 15 during dispensing. The piezoelectric material may be ceramic or an elastomeric (such as a polymer and/or copolymer based) material. If the piezoelectric material is located on an outside or inner surface, the surface may be configured to transfer the energy while inhibiting loss of the strength of the signal. In other embodiments, the inner surface may be configured to actually amplify the signal while in yet other embodiments, the signal takes into account the loss of the transmission through intermediate mediums and materials.

Figure 5A:
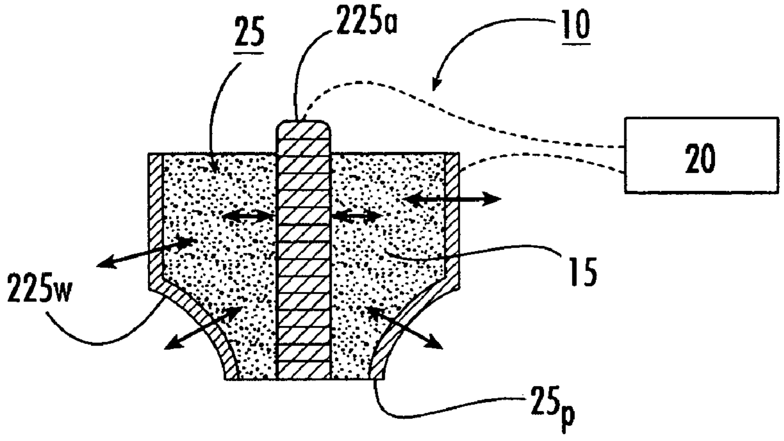
FIG. 5A is a partial section view of a dispensing system according to embodiments of the present invention.

FIG. 5A illustrates that a major portion of the length of the walls 225*w* that define the interior chamber of the hopper 25 can be piezoelectrically active. In other embodiments selective portions (illustrated by the cross hatch markings in FIG. 5A) can be formed to be piezoelectrically active. The selective portions may be continuous or segmented and spaced apart along the hopper 25. In certain embodiments, a series of radially and/or longitudinally spaced apart portions, other flow channel portions, or substantially the entire perimeter of a flow channel, can be made to be piezoelectrically active.

In addition, to increase the piezoelectric active surface area, at least one interior component 225*a* that comprises piezoelectric material can be disposed in the flow path. The interior component 225*a* may have a planar, spherical, cylindrical, or any other desired configuration. It may be fixed in the cavity of the hopper so that it is held in a static vertically position or may be dynamically mounted in the cavity. The entire perimeter of the interior component 225*a* may be active and able to flex, or selective portions or sides may be configured to flex. The interior component 225*a* may be rotatable or translatable (up, down, angularly, and the like) while also being able to flex in response to applied voltage or current. The interior component 225*a* and the walls 225*w* may be controlled by a single signal generator. Different signals, including signal line shapes, amplitudes of voltages, and the like may be applied at different locations so that the non-linear vibratory energy is cumulatively effectively transferred to the dry powder to facilitate fluid flow. In other embodiments, reciprocating voltage signal patterns or signals may be used (on opposing wall segments or between the intermediate component and a facing wall) to amplify the vibratory signal.

The signal 20*s* can be influenced by the amount of active surface and the excitation voltage pulses applied thereto as well as the channel geometry. During dispensing, the hopper and/or channel can be vibrated by providing a voltage across the piezoelectric layer. In certain embodiments, the voltage provided may be at about 100-200 volts peak-to-peak. In other embodiments, the voltage can be applied at a different level and at other various frequencies, such as at a higher frequency of between about 25 kHz to about 2 MHz.

In certain embodiments, the piezoelectric material, shown generally as element 225*w* in FIG. 5A can be formed from a piezoelectrically active material such as PVDF (known as KYNAR piezo film or polyvinylidene fluoride) and its copolymers or polyvinylidene difluoride and its copolymers (such as PVDF with its copolymer trifluoroethylene (PVDF-TrFe)). The piezoelectric material can be a thin flexible layer or film. The term "thin film" typically means that the layer has a thickness that is less than about 200 microns thick, and more typically less than about 100 microns thick (such as about 28 microns).

Non-vibratory insulating material (such as neoprene) can be disposed to hold the polymer and/or copolymer which can increase the interchange between the dry powder and the piezoelectric material; this may increase the amount of energy transferred to the dry powder from the oscillating or vibrating active piezoelectric polymer film so as to cause the dry powder to vibrate at a frequency that is at or near a resonant frequency thereof. In certain embodiments, laminates of one or more layers of PVDF and other material layers can be used. Suitable laminates include, but are not limited to, thin film layers of PVDF united to thin layers of one or more of aluminum, PVC and nylon films. The aluminum may help the channel hold its desired shape. The PVDF may form the bottom, top or intermediate layer of the laminate structure. For intermediate layer configurations, vias and/or edge connections can be used to apply the electric excitation signal.

In other embodiments, the piezoelectrically active material can be a ceramic. Examples of piezo-ceramic materials and elements are available from EDO Corporation, Salt Lake City, Utah. Generally described, piezoceramic materials can produce motion by receiving electric potential across their polarized surfaces. See Mostafa Hedayatnia, *Smart Materials for Silent Alarms,* Mechanical Engineering, at www.Memagazine.org/contents/current/features/alarms.html (©1998 ASME). Other piezo-electric materials can also be employed as long as they have sufficient structural rigidity or strength (alone or applied to another substrate) to provide the desired vibratory motion for the dry powder.

In certain embodiments, the hopper 25 can be shaped and/or sized to define a resonant chamber or cavity to generate a desired frequency of oscillation of the piezoelectric material and/or a particular dry powder formulation. That is, each blend or formulation of dry powder may exhibit different flow characteristics that can be accounted for in the geometry design of the hopper 25 and/or the applied signal. The height, depth, length, or width of the hopper flow path channel may be adjusted based on the particular dry powder being administered.

Metal trace patterns, where used, can be provided by applying a conductive pattern onto one or more of the outer faces of the piezoelectric substrate layer. For depositing or forming the metal, any metal depositing or layering technique can be employed such as electron beam evaporation, thermal evaporation, painting, spraying, dipping, or sputtering a conductive material or metallic paint and the like or material over the selected surfaces of the piezoelectric substrate (preferably a PVDF layer as noted above). Of course, alternative metallic circuits, foils, surfaces, or techniques can also be employed, such as attaching a conductive mylar layer or flex circuit over the desired portion of the outer surface of the piezoelectric substrate layer.

Generally described, for piezoelectric polymer materials, inner and outer surface metal trace patterns can be formed on opposing sides of the piezoelectric polymer material in a manner that provides separation (the opposing traces do not connect or contact each other). For example, conductive paint or ink (such as silver or gold) can be applied onto the major surfaces of the package about the elongated channels and associated metal traces such that it does not extend over the perimeter edge portions of the piezoelectric substrate layer, thereby keeping the metal trace patterns on the top and bottom surfaces separated with the piezoelectric substrate layer therebetween. This configuration forms the electrical excitation path when connected to a control system to provide the input/excitation signal for creating the electrical field that activates the deformation of the piezoelectric substrate layer during operation. The excitation circuit configuration can be such that the upper trace operates with a positive polarity while the lower trace has a negative polarity or ground, or vice versa (thereby providing the electric field/voltage differential to excite the piezoelectric substrate). Of course, the polarities can also be rapidly reversed during application of the excitation signal (such as + to –, or + to –) depending on the type of excitation signal used, thereby flexing the piezoelectric material in the region of the receptacle portion. For a more complete discussion of the active excitation path or configuration as used in forming blister packages, see U.S. Provisional Application Ser. No. 60/188,543 to Hickey et al., and corresponding International PCT publication WO 01/68169, the contents of which are incorporated by reference herein. In addition, the piezoelectric polymer material may be configured as two sandwiched piezoelectric polymer film layers separated by an intermediately positioned pliable core, all of which are concurrently deformable by the application of voltage thereacross.

Figure 5B:
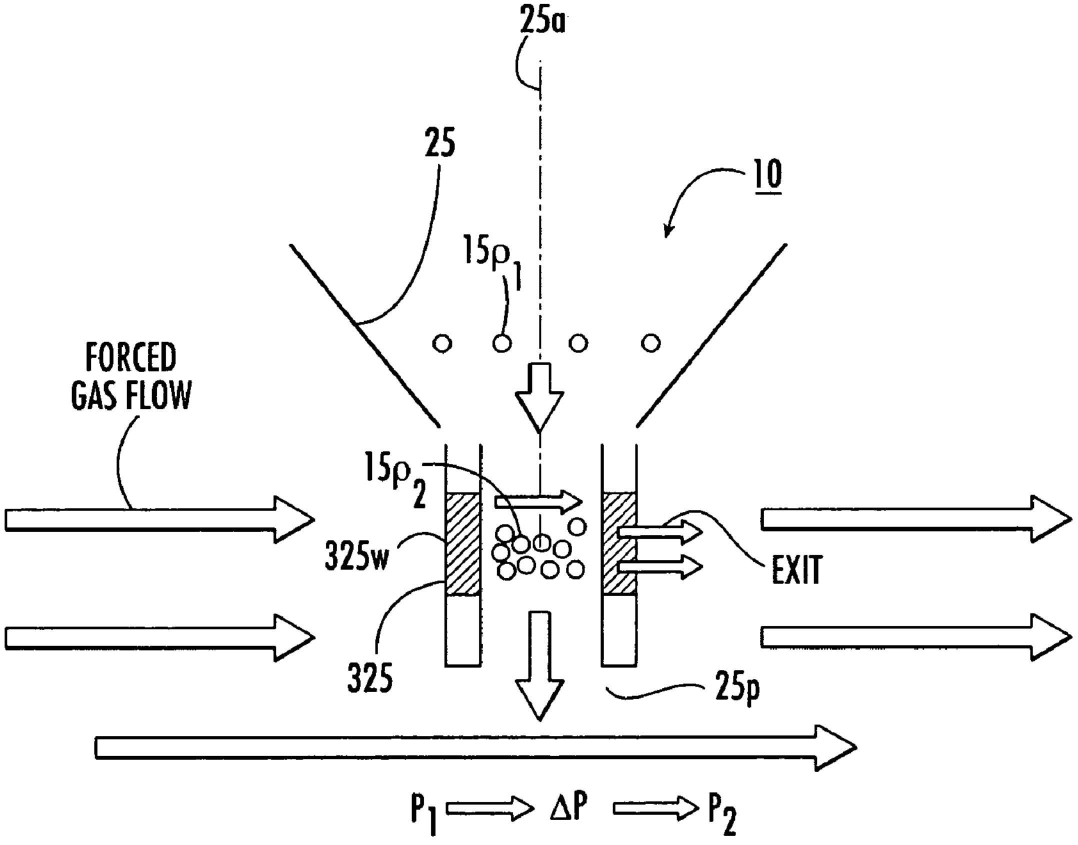
FIG. 5B is a partial section view of a dispensing system according to alternative embodiments of the present invention.

FIG. 5B illustrates an alternate embodiment of the present invention. In this embodiment, the bulk density of the dry powder is (temporarily) increased along the flow path during the flowing dispensing operation. As shown, the hopper 25 includes a permeable member 325 that forms a portion of the wall segment in the flow path. The bulk density 15ρ1 of the dry powder 15 above this segment is reduced (shown by fewer numbers of spaced apart particles) to the bulk density below or at this segment 15ρ2 (shown by a condensed or increased concentration of particles). The permeable member 325 is configured to receive pressurized gas at a first wall inlet region 325*i* and expel it at an egress portion 325*e* across from the receiving region 325*i* so that the forced gas travels across the dry powder and flow path as the dry powder is dispensed vertically at the port 25*p*. The pressure of the forced gas flow is higher at the inlet region than at the egress or outlet region 325*e*. This cross-travel provides a pressure drop that slightly compresses the dry powder to increase the apparent bulk density (making it heavier with a larger downwardly oriented Fv) to facilitate meted dispensing. In certain embodiments, the permeable member 325 is configured to direct an exogenous pressurized gas (such as air) to flow at substantially 90 degrees across the flow path while the dry powder is flowing downwardly in a manner that inhibits aggregation. This can temporally compress the dry powder to increase the bulk density of the dry powder.

The permeable member 325 can define a portion of the wall 325*w* of the flow path to provide a substantially continuous contour inner wall. The inlet region 325*i* and outlet region 325*e* may be horizontally symmetrically disposed about the axis of the flow path 25*a* (as shown) or may be vertically offset (not shown), such as with the egress portion below the inlet portion. In any event, the permeable member 325 is configured to generate a predominantly cross-flow forced air pattern. The desired entry pressure and pressure drop can be selected as a function of particle size, size distribution, porosity, and apparent density. In certain embodiments, the pressure can be provided at between about 1.10-5 atm and the pressure drop across the flow path (measured at the exit or egress region) can be less than 10-20%. In certain embodiments, the bulk density may be increased by about 10-100%.

In certain embodiments, the permeable member 325 can be a filter or stainless steel frit that is sized and configured to allow gas or air flow thereacross with a pore size that inhibits dry powder from exiting from same when exposed to the pressurized gas cross-flow. Other suitably configured materials and structures may also be used. Preferably, the permeable member 325 and the components defining the dry powder contact surfaces in the flow path of the dispensing system 10 are configured to dispense in vivo biocompatible formulations and to withstand periodic sterilization cleaning procedures. In other embodiments, portions of the flow path may be disposable after dispensing a suitable number of unit amounts to promote anti-aggregation improved flow and/or reduced-maintenance systems.

In certain embodiments, multiple vibratory inputs can be employed concurrently, alone or in combination with the non-linear sources. Thus, for example, the hopper and dispensing port have an associated axis extending along the gas flow path and the system can include a translation mechanism that moves at least a portion of the hopper in a desired motion, such as an eccentric motion, so that at least a portion of the hopper oscillates relative to the axis and, in operation, generates a force with a downward force component or vector that is transmitted to the dry powder during dispensing. In other examples, a portion of the hopper 25 (and/or each individual dispensing head 425*h*, see FIG. 9) may be exposed to centrifugal acceleration or other suitable motion to impart an angular velocity onto the dry powder held therein, thereby introducing downward force vectors, Fv, onto the dry powder during flow to compress the powder bed to increase the apparent bulk density and inhibit aggregation without requiring evacuation of the flowing (low density) powder.

FIG. 6 illustrates that the dispensing system 10 can be configured to operate with both non-linear vibration energy and centrifugal motion 20*m* (represented by the arrows dispersed about the axis 25*a*). The motion may be accomplished by moving, or oscillating, the hopper 25 about its axis 25*a*. In operation, the motion 20*m* can generate a force with a downward force component or vector that is transmitted to the dry powder during dispensing.

FIG. 7 illustrates one embodiment whereby local non-linear vibration energy can be applied to the dry powder 15. As shown, the hopper 25 includes a head portion 25*h* with an insert 31 held therein. The insert 31 can be configured as an elongated insert that is held in the flow path in the hopper 15 such that the insert 31 is pivotably and/or floatably held in the flow path and extends a distance out of the dispensing port 25*p* and rotates relative to the hopper 25 and the axis 25*a* during dispensing to transmit directional acceleration to particles of the dry powder 15. The dry powder 15 may be dispensed through the end portion of the insert 31. FIG. 8 illustrates that the insert 31' can be configured to define a flow path 25*f* and a dispensing port that is translated in a predetermined motion 20*s* about the axis 20*a*, during operation. In other embodiments, the insert 31, 31' may comprise outwardly extendable members that move up and down corresponding to their speed of translation (not shown).

In any event, the insert 31, 31' can be translated and/or oscillated with a selected motion that has an associated non-constant period or periods, or may have a cyclical constant period or periods. The insert 31, 31' may be oscillated relative to the axis 25*a* to generate a force with a downward component or vector Fv that is transmitted to the dry powder 15 during dispensing. The insert 31, 31' may also comprise portions formed of piezoelectrically active material that can be excited to generate vibration energy.

FIG. 9 illustrates yet another embodiment of a dispensing system 10. As shown, the system 10 includes a hopper 25 that is sized and configured as a central hopper 425 that feeds a plurality of dispensing heads 425*h*. Vibration energy can be applied to a rack of heads, filling from a single hopper 425*h*. The central hopper can be translated back and forth in non-linear or linear manner to vibrate the contents thereof (the motion shown by arrows and element number 425*m*). The individual heads 425*h* can also be translated (rotated about the axis or moved up, down, diagonally, or otherwise) in a desired linear or non-linear manner. In particular embodiments, the heads 425*h* may be translated to generate an angular velocity that is sufficient to give directional acceleration to the particles. The extremes of motion or travel of the hopper 425 and/or the heads 425*h* may be very small, particularly when carried out at high frequencies. Thus, it is contemplated that the vibration generation energy output can employ a high frequency motion applied onto a selected portion of the hopper 425, with the outer bounds of the physical motion of the hopper being small. The term “high frequency” means frequencies in the range of between about 1 kHz-1000 kHz, typically at between about 10-100 kHz with the small bounds of travel, including movement in the range of between about 50-500 mm, and typically about 1-100 mm, or even less.

Figures 10A, 10B:
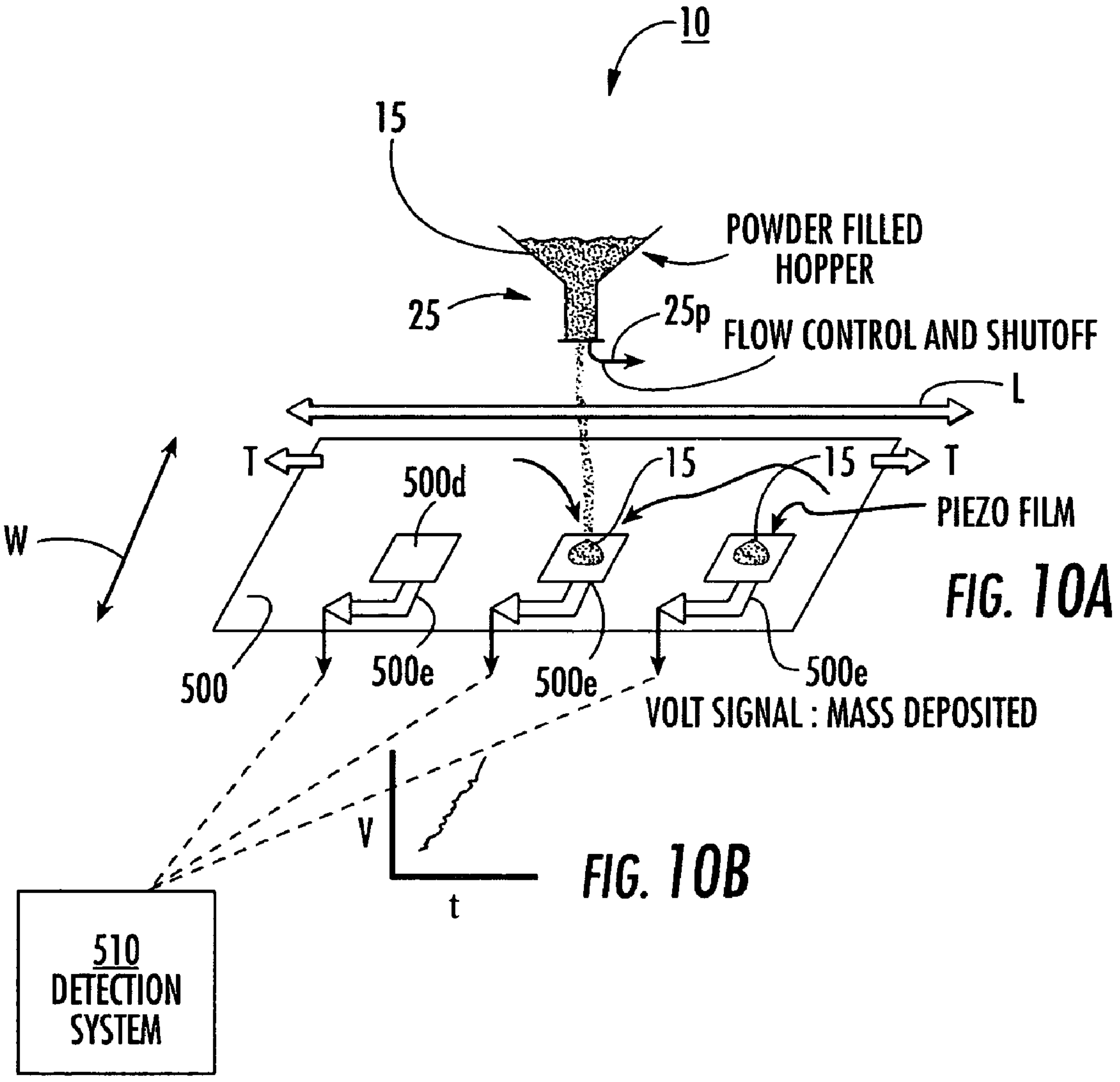
FIG. 10A is a schematic illustration of a dispensing system according to additional embodiments of the present invention.
FIG. 10B is a graph illustrating a detectable alteration in an electrical parameter that can be used to determine a dispensed mass or weight using a dispensing system similar to that shown in FIG. 10A according to embodiments of the present invention.

FIG. 10A illustrates a dispensing system 10 that cooperates with a sheet of receiving substrate material 500 that employs elastomeric piezoelectrically active material that can be used to measure small meted quantities of dry powders 15. As described for the piezoelectric material for the hopper 25 above, the piezoelectrically active substrate 500 can include a PVDF material. The PVDF material can be treated to have a metallic pattern 500*e* that can detect changes in a desired electrical parameter. One unitary sheet can be used with electrically isolated individual unit regions 500*d* or separate sheets can be used for each unit amount (not shown). The sheet 500 can be held in tension (along the length and/or width of the sheet) while a quantity of dry powder 15 is dispensed thereon. The tensioning may be provided by wrapping opposing end portions about tensioning bars that can be adjustably rolled to provide the desired tension. In other embodiments, the tensioning can be provided by tenting end portions of the sheet 500 over spaced apart structural members that may include a center support member (not shown). The sheets may have self-tensioning members that are portable therewith or tensioning members that are affixed to a conveying surface. Other tensioning mechanisms can also be employed as will be appreciated by one of skill in the art. Standard weighing techniques well known to those of skill in the art may also be used to determine the weight of the dispensed amount(s).

An alteration in a selected monitored electrical parameter that is induced by the weight residing on a unit region can be detected and a meted mass calculated by the amount of shift. The shift may be measured in a relative (pre and post change) or absolute amount (defining a pre-amount by a calibration number).

A detection system 510 can be configured to serially engage the unit regions on the sheet 500 or to simultaneously engage all of the receiving regions and selectively activate the detection to measure the desired location. The detection system 510 can be in communication with the dispensing system control system to provide dynamic real-time feedback data regarding the meted quantity that can be used to control the operation of the dispensing system. The data may be used to control the open time of gated flow paths that can be controlled to mete the desired amount. Over or under amounts, or departures from predetermined variability levels may be indicated when detected.

The detection system 510 may be configured to detect a change in capacitance or to obtain a plurality of voltage values (which may be transient) over time, during dispensing. Alternatively, the detection system 510 may be configured to detect after the dispensing. The induced change in the selected parameter or parameters is generated by the flexure or strain associated with the downwardly generated force associated with the weight of the dry powder on the stretched (tensioned) piezoelectrically active foil region 500*d*. Thus, the capacitance change and the like correspond to the deposited weight. The signal may be used to weigh or measure masses in the range of under about 30 mg, and typically under about 15 mg such as between about 10 μg-10 mg. Other electrical parameters may also be used such as, but not limited to, resonant frequency, and the like. Using the resonant frequency and/or capacitance parameter may provide increased sensitivity or resolution.

Figure 11:
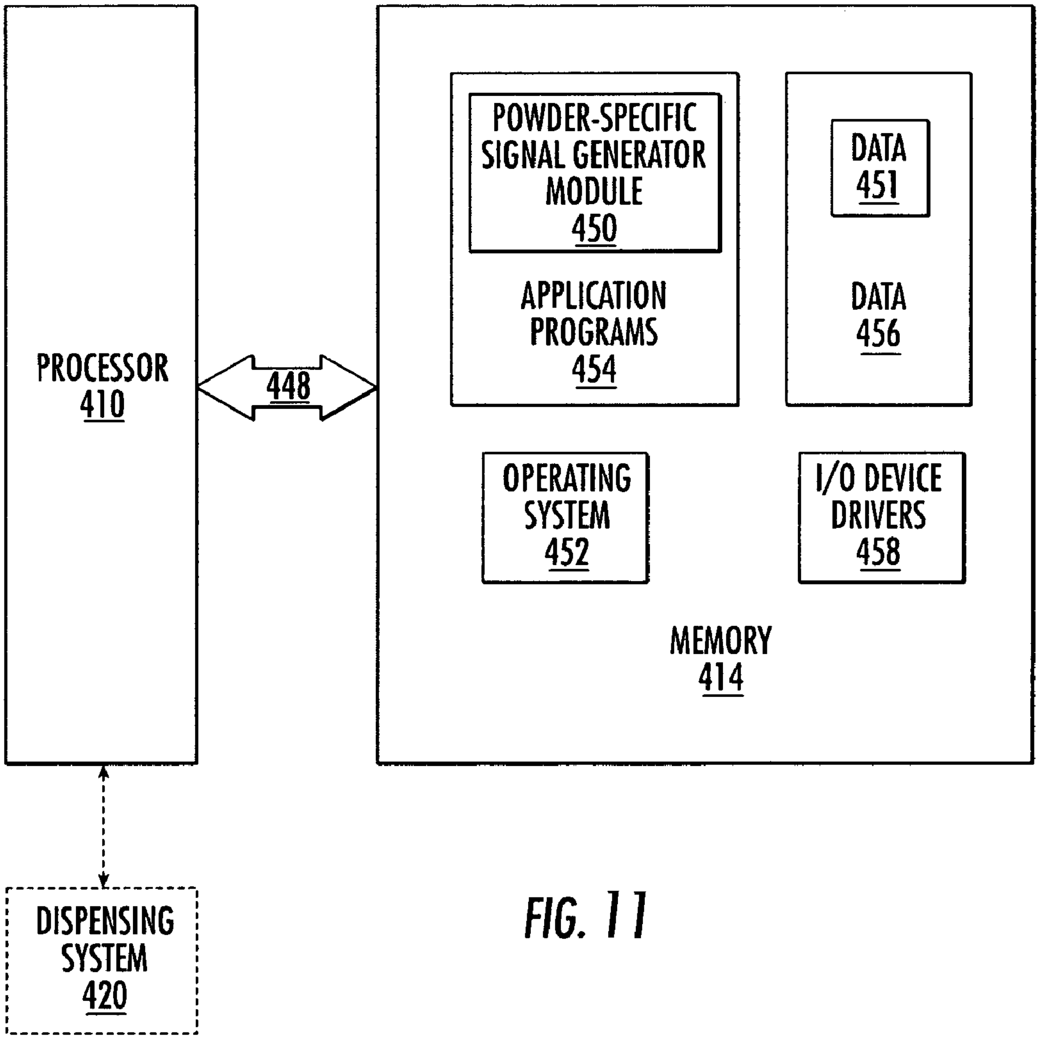
FIG. 11 is a block diagram illustrating a computer program module according to embodiments of the present invention.

FIG. 11 is a block diagram of exemplary embodiments of data processing systems that illustrates systems, methods, and computer program products in accordance with embodiments of the present invention. The processor 410 communicates with the memory 414 via an address/data bus 448. The processor 410 can be any commercially available or custom microprocessor. The memory 314 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 11, the memory 414 may include several categories of software and data used in the data processing system 405: the operating system 452; the application programs 454; the input/output (I/O) device drivers 458; the powder specific (vibratory) signal generator module 450; and the data 456. The data 456 may include a plurality of dry powder data 451 corresponding to particular or target signal parameters for each dry powder, which may be obtained from an operator or stored by the dispensing system 420 and/or timing data that defines the meted amounts, flow rates, and open time for the dispensing port (allowing automatic control of the dispensing operation, dependent on the dry powder being dispensed). As will be appreciated by those of skill in the art, the operating system 452 may be any operating system suitable for use with a data processing system, such as OS/2, AIX, OS/390 or System390 from International Business Machines Corporation, Armonk, N.Y., Windows CE, Windows NT, Windows95, Windows98 or Windows2000 from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components and/or the dispensing system 420.

The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the powder-specific signal generator module 450 being an application program in FIG. 11, as will be appreciated by those of skill in the art, other configurations may also be utilized while still benefiting from the teachings of the present invention. For example, the module 450 may also be incorporated into the operating system 452, the I/O device drivers 458 or other such logical division of the data processing system 405. Thus, the present invention should not be construed as limited to the configuration of FIG. 11, which is intended to encompass any configuration capable of carrying out the operations described herein.

In certain embodiments, the powder-specific signal generator module 450 includes computer program code for automatically determining the type of vibratory input desired to generate a non-linear vibratory energy signal directing the selective operation of the vibratory energy in and/or along the flow path according to the dry powder being dispensed.

The I/O data port can be used to transfer information between the data processing system 405 and the dispensing system 420 or another computer system or a network (e.g., an intranet and/or the Internet) or to other devices controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 11 but is intended to encompass any configuration capable of carrying out the operations described herein.

The flowcharts and block diagrams of certain of the figures herein illustrate the architecture, functionality, and operation of possible implementations of dry powder-specific dispensing, processing and/or vibratory energy excitation means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In certain embodiments, the system 10 can accept user input regarding the type of dry powder being processed and/or dispensed. The system 10 can be configured to accept manual or electronic input and production batches (with the desired dry powder to be dispensed) can be identified over a selected period of time and saved for automatic interrogation by the control module upon each new batch, shift, or other desired time interval.

In certain embodiments, the present invention can provide computer program products for operating a flowing dry powder dispensing system having an associated dry powder flow path with a dispensing port and a vibration energy source associated therewith to facilitate flow. The computer program product can include a computer readable storage medium having computer readable program code embodied in said medium. The computer-readable program code including: (a) computer readable program code that identifies at least one, typically a plurality of different, powder-specific (flow enhancing) vibration energy signals (where there are a plurality, a respective one can be supplied for each of the plurality of different dry powders), the vibration energy signal(s) corresponding to individually predetermined flow property data of the plurality of dry powder(s); and (b) computer readable program code that directs the system to operate using the powder-specific vibration energy signal associated with the dry powder being dispensed (that can be selected from a library of pre-identified selectable versions of the plurality of different vibration energy signals).

In certain embodiments, the powder specific vibration energy signals are non-linear. The computer program code can accept user input to identify the dry powder being dispensed, and computer program code that automatically selectively adjusts the output of the vibration energy signal based on the identified dry powder being dispensed. The vibration energy output signals for the dry powders being dispensed are based on data obtained from a fractal mass flow analysis or other suitable analysis of the different dry powders.

The output signals may be include a plurality, typically at least three, superpositioned modulating frequencies and a selected carrier frequency. The modulating frequencies can be in the range noted herein (typically between about 10-500 Hz), and, in certain embodiments may include at least three, and typically about four superpositioned modulating frequencies in the range of between about 10-100 Hz, and more typically, four superpositioned modulating frequencies in the range of between about 10-15 Hz.

The computer program code can controllably dispenses meted quantities of dry powder independent of volumetric evaluations by considering flow rate of the dry powder out of the dispensing port and controlling the amount of time the dispensing port is open during dispensing.

Figure 12:
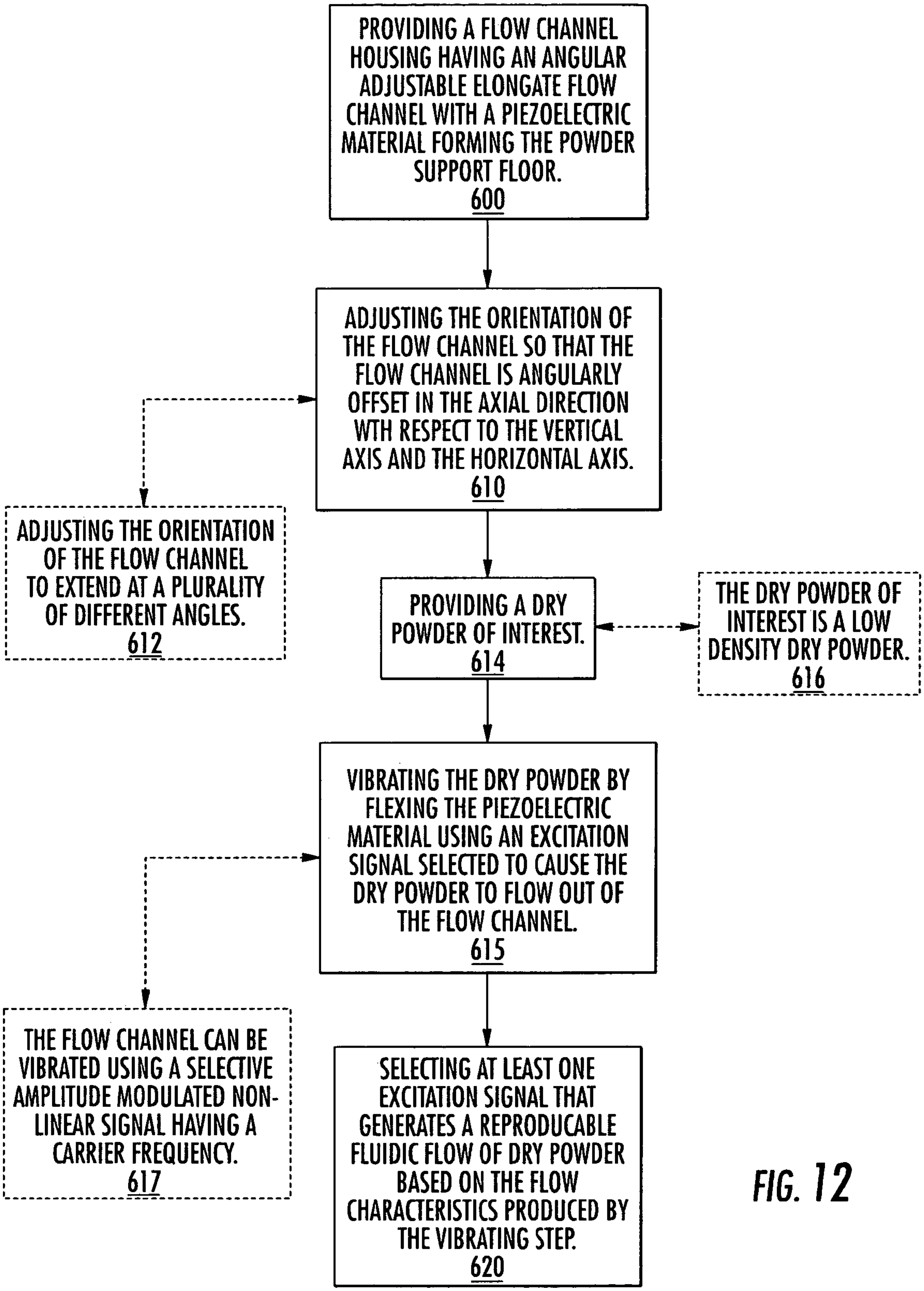
FIG. 12 is a block diagram of operations that can be used to evaluate dry powder dispensing parameters according to embodiments of the present invention.

FIG. 12 illustrates operations that can be carried out to evaluate or selected desired dispensing signals and/or system configuration parameters that can then be used to dispense target dry powders according to embodiments of the present invention. These operations can be used to determine the powder specific (vibratory) signal(s) of different target dry powders, the powder specific signal can then be implemented in a vibratory signal generator computer module for operating signal generators for dispensing a dry powder of interest.

As shown in FIG. 12, a flow channel housing having an angularly adjustable elongate flow channel therein is provided (block 600). The orientation of the flow channel is adjusted so that the flow channel is angularly offset (with the dispensing port located lower than the input port) in the axial direction with respect to the horizontal and vertical axis (block 610). In certain embodiments, the flow channel is adjusted to be at different selected angles during the evaluation to consider the impact that the angle may have on the dispensing flow.

A dry powder of interest is introduced into the elongate flow channel (block 614). The dry powder can be a low-density dry powder (block 616). The flow channel can be vibrated to thereby vibrate the dry powder to cause the dry powder to fluidly flow out of the channel via an exit port (block 615). The flow channel can include a flexible piezoelectric polymer over which the dry powder flows; the piezoelectric polymer can be electrically stimulated to flex upwardly to cause it to vibrate the powder as the powder travels along and through the flow channel. As described above, the vibration can carried out using a non-linear excitation signal having a carrier frequency and a modulation frequency (block 617). In certain embodiments, the carrier frequency can be between about 2.5 kHz-50 kHz and modulation frequency may be between about 10-500 Hz. In any event, flow characteristics can be evaluated, typically over several different input signals at different frequencies, and at least one frequency (and/or angular orientation of the flow path) selected for its ability to generate reproducible fluidic flow of dry powder based on the flow characteristics exhibited during the vibrating step (block 620).

To generate sufficient flow in the flow channel to allow evaluation and/or reliable dispensing, a dry powder mass input of between about 2-50 mg or greater may be used to provide fluid flow through the dispensing port.

The apparatus can be configured to generate a reproducible flow rate with less than about +/−10% variation, typically less than 5% variation, and in certain embodiments, less than about 2% variation, for dispensing reliable amounts of dry powders.

The average flow rate generated for certain low-density dry powders may be in the range of between about 0.001-5 mg/sec. In certain embodiments, the flow rate may be about 0.028 mg/sec. In other embodiments, typically for unit and/or medium density (or greater density) powders, the flow rate may be greater, such as above 5 mg/sec to about 50 mg/sec or greater. For example, for medium density powders, the flow rates may typically be between about 10-30 mg/sec. In particular embodiments, the apparatus can be configured to dispense or process different dry powders, with typical flow rates between about 0.001-50 mg/sec or even greater, and typical flow rates for certain embodiments being between about 0.001-30 mg/sec. The greater flow rates typically correspond to the increased density dry powders (such as medium or greater density powders).

Several parameters can influence the dispensing flow rate, such as, but not limited to, the amount (mass) of dry powder input into the flow channel, the angle of the flow channel, the size of certain components, such as the surface area of the piezoelectric material that contacts the dry powder, the channel and/or orifice volumetric size (particularly the depth and width of the channel), the dry powder itself, as well as the vibratory signal input to excite the powder to move it through the flow channel can influence.

FIG. 13 illustrates a dry powder dispensing apparatus 700 that can be used to dispense dry powders. The apparatus 700 can be used at a laboratory and/or research site using flow parameters or signals that can generate fluidic flow for a dry powder of interest. In other embodiments, the apparatus 700 can be used in a scientific, research or small-scale academic and/or commercial program. For example, the device 700 can be used where it is desired to provide or dispense reliable amounts without need for mass production ramp-up for scaled commercialization. Thus, the apparatus 700 may be used to provide discrete amounts in desired reliable amounts (which, in certain embodiments, may be in the 50 μg-10 mg range), but larger or smaller amounts can also be provided, without requiring relatively expensive equipment costs and/or in a manner that is not labor intensive. In other embodiments, the apparatus 700 can be used to develop signals that are matched to a particular dry powder. The signal(s) can then be implemented using the same or a different dispensing apparatus, such as those described above, at a desired dispensing location.

Referring back to FIG. 13, the apparatus 700 includes a channel member 710, a cover member 720, and an intermediately positioned flexible piezoelectric polymer layer 730. The channel member 710 holds an elongate powder flow channel **710*f* that has a depth, width, and length. The piezoelectric polymer layer 730 can be positioned to overlie the channel 710***f* and the sidewalls to hold the dry powder as it moves through the flow channel 710*f*. Suitable materials for forming the flexible piezoelectric polymer layer 730 can be obtained from Measurement Specialties, Inc. located in Fairfield, N.J. One example of a suitable material is a 28 micron piezoelectric film sheet, silver ink metallized PVDF, identified as Part No. 1-100-4346-0. The piezoelectric polymer layer can include additional material layers attached thereto and/or coatings disposed thereon.

Figures 14A, 14B, 14C:
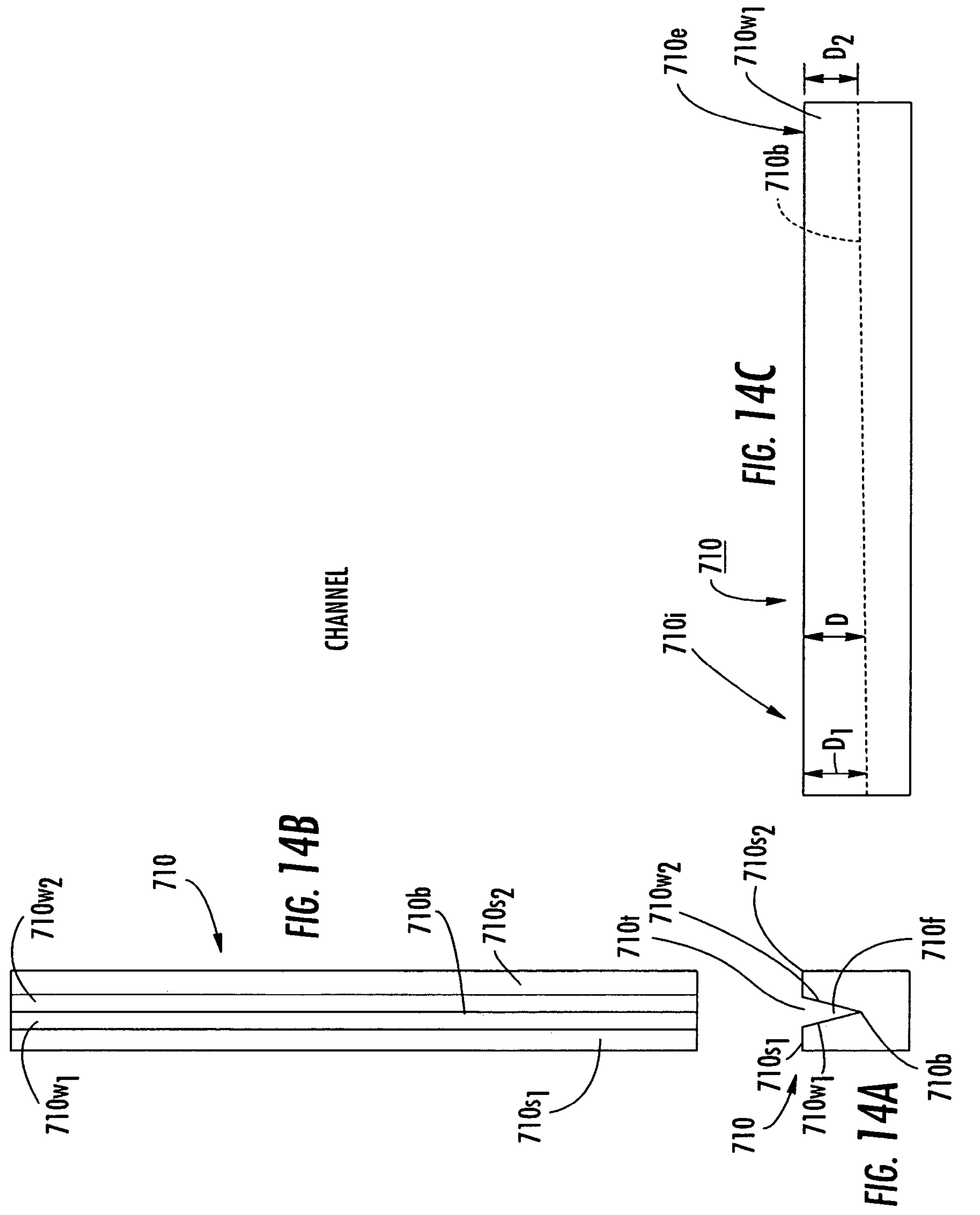
FIG. 14A is a front view of a flow channel member according to embodiments of the present invention.
FIG. 14B is a top view of the flow channel member shown in FIG. 14A.
FIG. 14C is a side view of the flow channel member shown in FIGS. 14A and 14B.

FIGS. 14A-14C illustrate one embodiment of a channel member 710. As shown in FIG. 14A, the flow channel 710*f* has two opposing sides 710*$w_1$*, 710*$w_2$* and may be configured with declining sides (each side converging toward the bottom of the channel from top to bottom). In particular embodiments, the flow channel 710*f* may have a sectional profile that is substantially a "V" shape, with the walls 710*$w_1$*, 710*$w_2$* angling to meeting at a common center located at a lowermost portion of the channel 710*b*. The depth of the channel can be less than about 5 cm, typically about 3.6 cm, or even less. Other configurations of the flow channel can be used, such as, but not limited to, concave, semi-circular, partial oval or partial elliptoid, frustoconical, and the like. Other channel depths may also be employed, depending on the scale, size of components, dry powder being dispensed and/or analyzed, and input used to carry out the vibration. The cover member 720 may be adjusted accordingly.

The channel member 710 may be configured with an open top portion 710*t* and opposing side edge portions 710*$s_1$*, 710*$s_2$*. FIG. 14C illustrates that the flow channel has a depth D that varies along the length of the flow channel 710*f*. As shown, the deepest portion of the flow channel $D_1$ is positioned proximate the dry powder intake (inlet port), while the more shallow depth $D_2$ is positioned proximate the dispensing port 725*p* (FIG. 13). The depth of the flow channel 710*f* can vary in a gradual manner, such as linearly (in a straight line) with a predefined slope.

In particular embodiments, the channel 710*f* can have a depth $D_1$ that is about 17 mm at the inlet portion 710*i* of the member 710 and terminates at a depth $D_2$ that is about the same at the exit portion 710*e*. The channel 710*f* may have a length that is less than about 20 cm. In certain embodiments, the channel has a length of about 13.1 cm. The width may be less than about 5 cm, and typically about 2 cm.

Figures 15A, 15B, 15C, 15D:
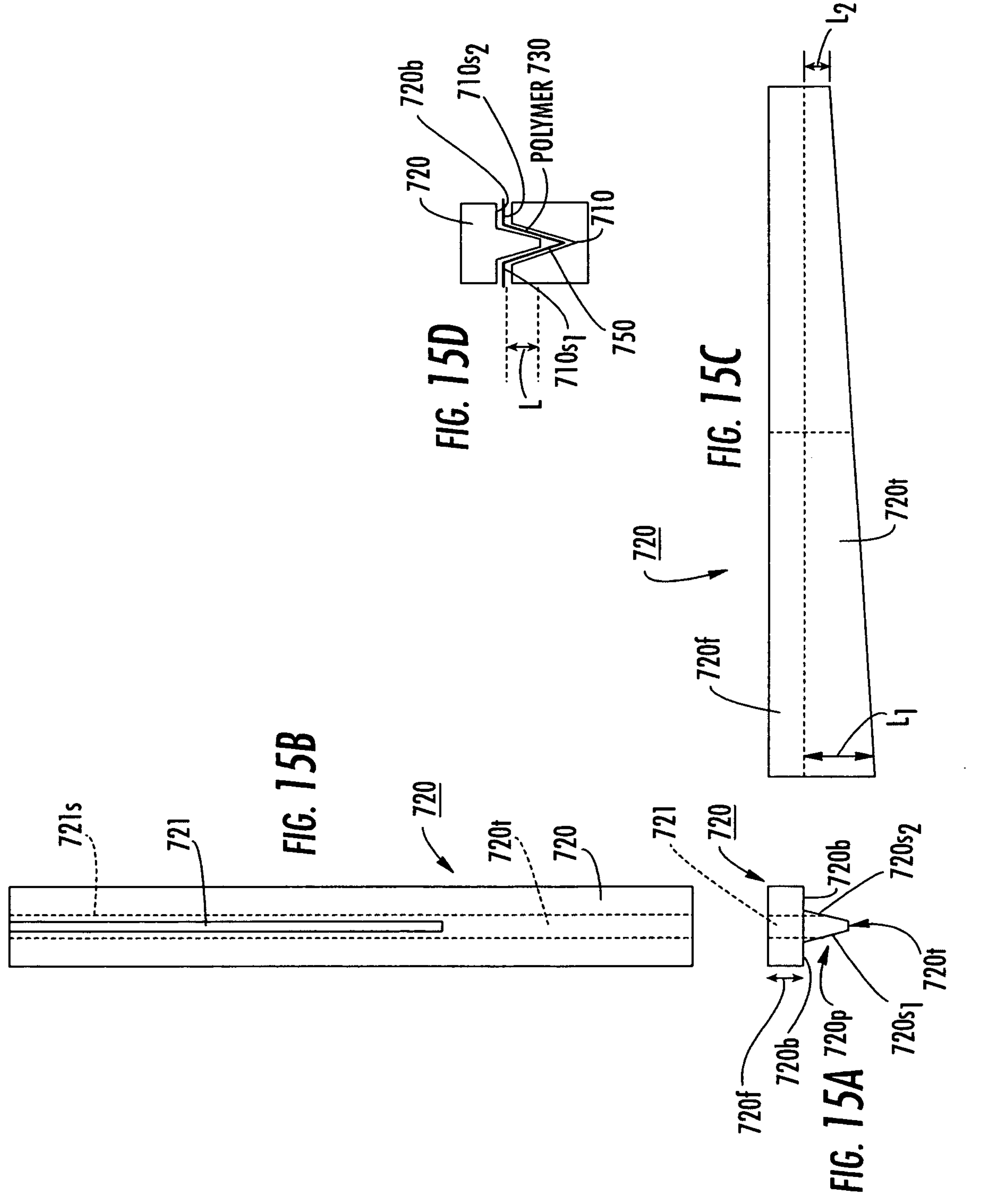
FIG. 15A is a front view of a cover member according to embodiments of the present invention.
FIG. 15B is a top view of the cover member shown in FIG. 15A.
FIG. 15C is a side view of the cover member shown in FIGS. 15A and 15B.
FIG. 15D is a front view of the cover member shown in position overlying the flow channel member of FIG. 14A according to embodiments of the present invention.

FIGS. 15A-15C illustrate one embodiment of a cover member 720. As shown in FIG. 15D, the cover member 720 is sized and configured with a tip portion 720*t* that, when assembled to the flow channel member 710, enters a distance "L" into the flow channel 710*f* of the channel member 710. As such, the tip portion 720*t* is sized and shaped to be able to be received into the flow channel 710*f*. As shown, the tip portion 720*t* includes sidewalls 720*$s_1$*, 710*$s_2$* that decline at the same angle as that of the walls 710*$w_1$*, 710*$w_2$* of the channel member 710. Because the cover member 720 has a flange 720*f* of substantially constant thickness that sits on the upper portion of the flow channel member 710, the length of the tip portion 720*t* defines its penetration depth into the flow channel 710*f*. The tip portion 720*t* can be sized so that, in position, its lowermost portion does not contact the bottom 710*b* of the flow channel 710*f* so as to provide an open flow orifice and inhibit pinching the piezoelectric layer 730 between the two members 710, 720.

As shown in FIG. 15D, the cover member 720 includes a bottom portion 720*b* that is configured to reside on the upper side edge portions 710*$s_1$*, 710*$s_2$* of the channel member 710 to position the tip portion 720*t* of the cover member the desired distance into the depth of the flow channel 710*f*. The space extending between the tip portion 720*t* of the cover member 720 and the piezoelectric layer 730 extending over the bottom 710*b* of the flow channel 710*f* can be defined as the flow orifice 750. Thus, when assembled, the open flow orifice 750 proximate the dispensing outlet or port (or dispensing end of the device) can vary a desired amount. In certain embodiments, the variation is from about 2 mm-7 mm, and in other embodiments about 2-5 mm.

FIG. 15D illustrates the cover member 720 positioned over the flow channel member 710 with the piezoelectric layer 730 held therebetween. The assembled members 710, 720 define a gap distance (or flow orifice) between the lowermost portion of the tip portion 720*t* of the cover member 720 and the lowermost portion of the flow channel 710*b*. This gap distance can be adjusted by sliding the cover member 720 forward or rearward in the flow channel member 710.

As shown in FIG. 15C, the vertical or inward projection length of the tip portion 720*t* can vary over the axial length of the cover member 720. This allows for the device to adjust the size of the reservoir defined by the coupling of the cover member 720 to the flow channel member 710.

Figure 17A:
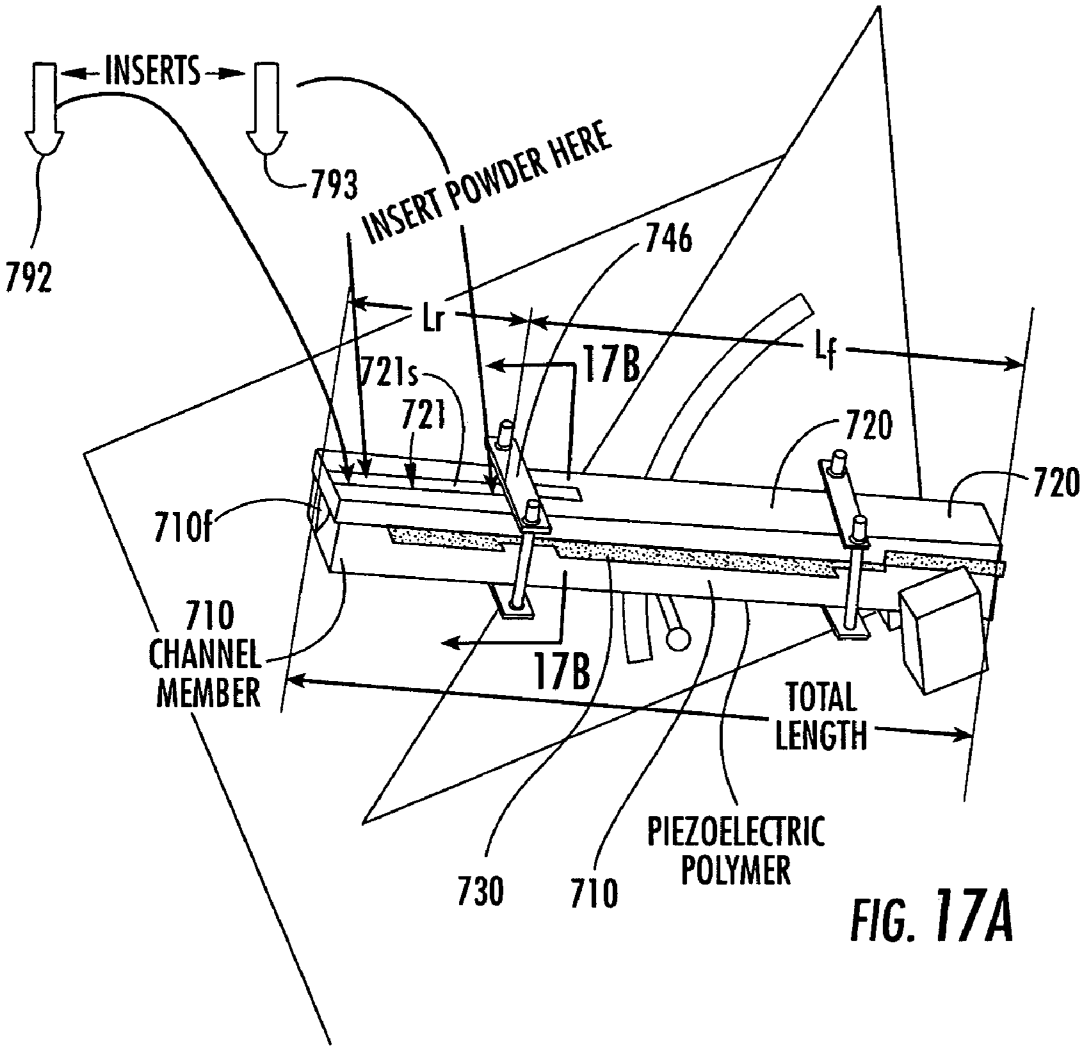
FIG. 17A is a perspective view of an alternate embodiment of a dispensing and/or dry powder flow evaluation apparatus according to embodiments of the present invention.
Figure 17B:
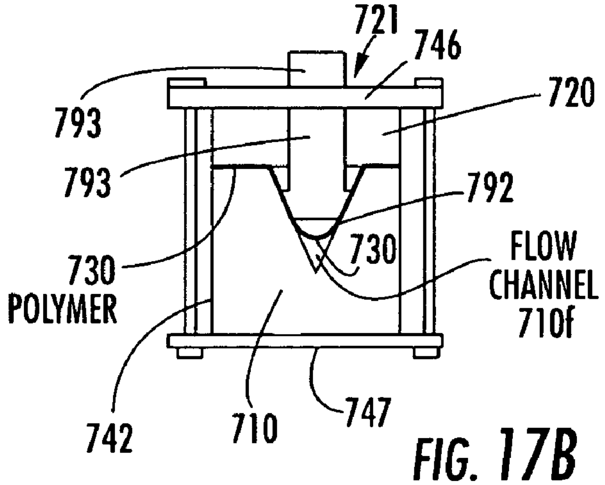
FIG. 17B is a section view of the device taken along line 17B-17B in FIG. 17A.

As shown in FIGS. 15D and 17B, the piezoelectric material layer 730 can be tensioned across opposing sides of the flow channel 710*b* so that its center portion is free to flex in response to the applied excitation (vibratory) signal. The outer edge or perimeter portions of the piezoelectric material 730 can be pinched or clasped between the overlying members 710, 720.

In operation, the piezoelectric layer 730 flexes upwardly in response to the input excitation signal(s) to vibrate the powder positioned above the piezoelectric layer 730. When non-conductive cover members are employed (such as those formed of DELRIN polymer), aluminum foil can be positioned over the tip portion 720*t* of the cover member 720 to inhibit static build up in the dry powder. In other embodiments, the cover member 720 may be formed of a pharmaceutically compatible conductive material, such as stainless steel, and/or the appropriate surfaces can be coated with a desired metallic coating, such as gold. In certain embodiments, an ionizer bar can be placed at one or more positions in the flow channel to decrease the static charge, suitable ionizer bars are available from NRD, LLC, located in Grand Island, N.Y.

FIG. 15B illustrates that the cover member 720 can have an elongate dry powder input region 721 that is open to the channel member 710 below. Thus, in operation, the dry powder can be input at desired locations over the channel 710*f* even if the cover member 720 is slid (rearward or forward) a distance over the flow channel 710*f* for adjustment of the flow orifice size. The length of the input region 721 (slot 721*s*) may be at least about 2.9 cm. As shown in FIGS. 17A and 17B, the flow channel 710*f* can be divided into a reservoir length $L_r$ and an adjacent flow channel length $L_f$. The reservoir length is that portion of the flow channel in the inlet region 721 that is defined between two inserts 792, 793. The inserts 792, 793 are sized to extend through the cover member slot 721*s* a depth into the channel. As shown in FIG. 17B, the first or upstream insert 792 has a greater length than the downstream insert 793 and is configured to extend to contact or force the piezo-layer 730 to move closer to the bottom of the channel 710*f* and inhibit backflow of the powder in the reservoir so as to hold a dry powder material supply in the inlet region 721 and gradually feed the dry powder into the flow channel length $L_f$. The flow channel length $L_f$ can be described as that portion of the flow channel 710*f* that is located downstream of the reservoir (downstream of a major portion of the input region 721, shown as downstream of the first bracket 746).

Figure 16B:
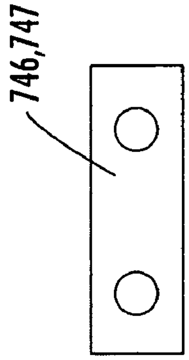
FIG. 16B is a top view of a clamping brace that may be used to secure the cover member (FIG. 15A) and flow channel member (FIG. 14A) according to embodiments of the present invention.
Figure 16A:
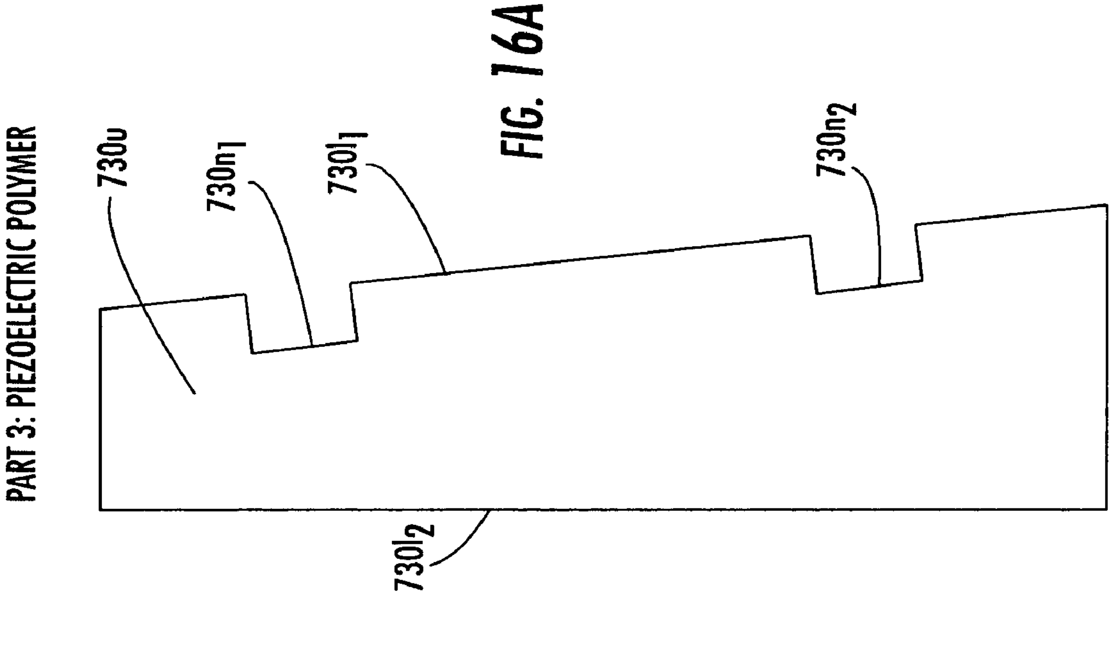
FIG. 16A is a top view of a piezoelectric polymer member according to embodiments of the present invention.

FIG. 16A illustrates one embodiment of a configuration of a piezoelectric layer 730 that may be a piezoelectric polymer layer. It is noted that the term "piezoelectric polymer layer" is used for ease of description, but the term "polymer" can also include co-polymers and blends, mixtures and derivatives thereof. As shown, one long side 730*l* of the layer 730 has a flap portion 730*f* with cut outs 730$n_1$, 730$n_2$ which are configured to allow upwardly extending attachment members 742, 743 (FIG. 13) to extend therethrough. The other side 730$l_2$ can be substantially straight and configured to be substantially flush between the aligned portions of the cover member 720 and flow channel member 710. The attachment members 742, 743 can be used to attach upper and lower bracket pairs 746, 747, which clamp the cover member 720 and flow channel member 710 together. The cover member 720 can be formed with sufficient weight to obviate the need for clamping, or other attachment means can be used to provide the desired holding force to keep the layer 730 in position. The flexible piezoelectric layer 730 can be preformed or formed in situ to substantially conform to the shape of the underlying channel 710*f*. The position of the cover member 720 and the length of the associated tip projection 720*t* can influence the size of the flow orifice provided by the cooperation of the layer 730 and the cover and flow channel members 720, 710, respectively.

As shown in FIG. 13, the layer 730 is pinched or securely held about its perimeter portion. However, the layer 730 is held in the channel 710*f* so that its primary surfaces are able to flex upwardly. The piezoelectric layer 730 is held so that the portion of the layer 730 in the flow channel 710*f* is forced to vibrate in the upward direction. As shown in FIG. 13, the signal(s) can be applied directly to the piezoelectric layer 730 from a signal generator 20 via a signal lead 775.

Referring again to FIG. 13, an amplifier 20A can be operatively associated with the signal generator 20 and used to modulate the signal before transmitting to the layer 730, as desired. The signal generator 20 can be any suitable signal generator. In certain embodiments, the signal generator 20 is a wave signal generator that can incorporate or be operatively associated with an amplifier. The signal generator 20 may be combined into a signal processor or provided by other configurations of electronic circuitry. In certain embodiments, the ground connection can be via the top surface of the polymer layer 730 with the positive contact via the bottom surface. The metallization can be removed from the region to which the ground connects. Positioning the ground connection on the top surface (where the dry powder resides) can act to inhibit the dry powder being exposed to voltage during operation. The electrical contacts can be made via a central portion of the flap 730*f*, although other locations may also be used.

Valves or other "on-off" configurations can be used to dispense discrete amounts of the dry powder. In certain embodiments, the flow dispensing can be controlled by terminating and/or electrically decoupling the input signal from to the piezoelectric layer 730 such as by using timer 20*t*. As described above for other embodiments, the receiving containers may be translated under the dispensing orifice at a timed rate to provide the desired amounts. In certain embodiments, a plurality of elongate flow channels can be arranged to concurrently and/or serially dispense (the same or different) dry powder (not shown).

As shown in FIG. 13, the apparatus 700 may include an angle adjustment mechanism 780. As shown, the angle adjustment mechanism includes a bracket 780*b* upon which a portion of the underside of the flow channel member 710 can rest. The apparatus 700 can include a hinge bracket member 745 that is pivotably attached to a portion of the flow channel member 710 (and/or cover member 720). In operation, the bracket 780*b* can be raised and lowered and the flow channel member 710 pivots accordingly to adjust the angle of inclination of the flow channel 710*f*. As will be appreciated by one of skill in the art, other angle adjustment configurations can be employed. The angle adjustment mechanism 780 can include a protractor or other angular scale to allow a user to be able to ascertain the angle without undue measurement. Typically, during evaluation of a powder, when the apparatus 700 is used to ascertain flow parameters, the flow channel 710*f* will be positioned at several different angles. In certain embodiments, the angles evaluated can be proximate to but under the static angle of repose (under or over 90 degrees), and may, in certain embodiments, be between about 10-75 degrees.

The frequency of the signal generated to cause the selected vibration to obtain the desired fluidic flow is typically influenced by the voltage amount per frequency per given capacitance. As the polymer layer defines the capacitance, the size of the layer or sheet will influence this parameter. In addition, the amplifier selected may also limit the operational frequency of the wave signal generator employed. Off the shelf units (such as a 200V amplifier) may limit the amplitude modulated (carrier) frequency output to between about 2500-7800 Hz, while customized signal processors may not be so limited (capable of generating increased carrier frequencies in the range of between about 15 kHz-50 kHz, or more as described above). An example of suitable waveform generator is Part No. 33120A from Agilent, located in Palo Alto, Calif., and a suitable amplifier is Part No. EPA-104 from Piezo Systems, located in Cambridge, Mass.

The apparatus 700 can include a stationary mounting frame 790 that holds the angle adjustment mechanism 780, the hinge bracket member 745, and the flow channel and cover members 710, 720, respectively.

As shown in FIG. 13, the apparatus 700 may include a hopper 25 with a hopper outlet port 25*p* that is in fluid communication with the cover member port 721 that can continuously or episodically feed dry powder into the flow channel 710*f*.

Although particularly suitable for pharmaceutical dry powders, the methods, systems and devices contemplated by the present invention may be used to dispense any desired dry powder, such as toners and the like.

The invention will now be described in more detail in the following non-limiting examples.

EXAMPLE 1

The data in Tables 2 and 3 were obtained using the apparatus illustrated in FIG. 13. The signal generator was a 200V amplifier. The carrier frequency selected for the Inhalac 230 dry powder (a dry powder from Meggle Gmbh, Wasserburg, Germany, that has a 230 mesh size when sieved by the manufacturer) was 7500 Hz. The signal (identified as arb 2 signal) used to vibrate the piezoelectric polymer layer may be formed and/or expressed using one or more of Equations 1-6 herein. The exemplary excitation signal includes the superposition of four modulating frequencies ranging from 10-15 Hz.

Mass Flow Rate Data for Inhalac 230

| Conditions | |
|---|---|
| Mass in reservoir (mg) | 350 |
| Channel Angle (deg.) | 24 |

-continued

| Mass Flow Rate Data for Inhalac 230 | |
|---|---|
| Conditions | |
| Carrier Freq. (Hz) | 7500 |
| Signal | arb2 |
| Powder | Inhalac 230 |
| primed (s) | ~60 |

| delta t (s) | mass (mg) | mass flow rate (mg/s) |
|---|---|---|
| 3 | 9.57 | 3.190 |
| 3 | 9.77 | 3.257 |
| 3 | 9.74 | 3.247 |
| 3 | 10.86 | 3.620 |
| 3 | 10.46 | 3.487 |
| AVG | | 3.360 |
| ST DEV | | 0.184 |
| RSD | | 5.5% |

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of flowably dispensing or processing dry powders from a device having a dry powder flow path, comprising:

generating a first non-linear vibration input signal, the first non-linear input signal comprising a carrier frequency modulated by a plurality of different selected frequencies that correspond to a first non-pharmaceutical dry powder formulation;

applying the first non-linear vibration input signal to a portion of a dry powder flow path while the first dry powder formulation is flowing therethrough; and providing a second non-pharmaceutical dry powder and mixing the first and second dry powders based on the generating and applying steps.

2. A method of flowably dispensing or processing dry powders from a device having a dry powder flow path, comprising:

generating a first non-linear vibration input signal, the first non-linear input signal comprising a plurality of different selected frequencies that correspond to a first non-pharmaceutical dry powder formulation;

applying the first non-linear vibration input signal to a portion of a dry powder flow path while the first dry powder formulation is flowing therethrough;

generating a second non-linear vibration input signal, the second non-linear input signal comprising a plurality of different selected signal frequencies that correspond to predetermined flow characteristics of a second non-pharmaceutical dry powder formulation; and applying the second non-linear vibration input signal to the flow path while the second non-pharmaceutical dry powder formulation is flowing therethrough, the second input signal being different from the first input signal.

3. A method of flowably dispensing or processing dry powders from a device having a dry powder flow path, comprising:

generating a first non-linear vibration input signal, the first non-linear input signal comprising a carrier frequency modulated by a plurality of different selected frequencies that correspond to a first non-pharmaceutical or pharmaceutical dry powder formulation; and applying the first non-linear vibration input signal to a portion of a dry powder flow path while the first dry powder formulation is flowing therethrough, wherein the vibration input signal comprises imparting a high frequency motion onto a selected portion of a hopper in the flow path, with outer bounds of a motion induced by the vibration input of the hopper is small.

4. A method of flowably dispensing or processing dry powders from a device having a dry powder flow path, comprising:

generating a first non-linear vibration input signal, the first non-linear input signal comprising a carrier frequency modulated by a plurality of different selected frequencies that correspond to a first non-pharmaceutical or pharmaceutical dry powder formulation; and applying the first non-linear vibration input signal to a portion of a dry powder flow path while the first dry powder formulation is flowing therethrough, wherein the first non-linear vibration input signal is generated using a plurality of superpositioned modulating frequencies, and wherein the number of superpositioned modulating frequencies is at least three.

5. A method according to claim 4, wherein the number of superpositioned modulating frequencies is four.

6. A method according to claim 5, wherein the four modulating frequencies are in the range of between about 10-15Hz.

7. A method of operating a dry powder filling system for dispensing non-pharmaceutical formulations of dry powder substances, comprising:

generating a vibratory signal comprising a carrier frequency modulated by a plurality of selected frequencies, wherein the selected frequencies corresponding to identified a priori flow characteristic frequencies of a non-pharmaceutical dry powder;

applying the vibratory signal to a dry powder in a dispensing flow path of a bulk powder enclosure; then dispensing meted quantities of the dry powder from the dispensing flow path during the applying step, wherein the a priori flow characteristic frequencies correspond to observed frequencies in an avalanche-analysis spectrum of the dry powder, and wherein the non-linear vibratory signal "$x_{signal}$" is a cumulative signal that comprises a sum of selected observed frequencies derived from an avalanche-analysis spectrum of the dry powder.

8. A method according to claim 7, wherein the non-linear input signal "$x_{signal}$" is derived from a mathematical equation:

$$x_{signal}=xf_2+xf_3+xf_4+\ldots xf_n$$

where said $f_2$, $f_3$, $f_4$ . . . $f_n$, respectively, correspond to most observed frequencies in an avalanche-based analysis spectrum of the dry powder and said "x" used with $f_2$, $f_3$, $f_4$, $f_n$, is a variable representing amplitude weight for a respective observed frequency.

9. A method according to claim 8, wherein one or more of said xf2, xf3, xf4, . . . xfn is multiplied by a phase adjustment.

* * * * *

UNITED STATES PATENT AND TRADEMARK OFFICE

CERTIFICATE OF CORRECTION

PATENT NO. : 7,677,411 B2
APPLICATION NO. : 10/606676
DATED : March 16, 2010
INVENTOR(S) : Crowder et al.

It is certified that error appears in the above-identified patent and that said Letters Patent is hereby corrected as shown below:

On Title Page:
Item 54, Title: Please correct "EVALUATINGL" to read -- EVALUATING --

Column 1, Line 3: Please correct "EVALUATINGL" to read -- EVALUATING --

Signed and Sealed this

Third Day of August, 2010

David J. Kappos
*Director of the United States Patent and Trademark Office*